US006475754B1

(12) United States Patent
Bemis et al.

(10) Patent No.: US 6,475,754 B1
(45) Date of Patent: Nov. 5, 2002

(54) **POLYNUCLEOTIDES ENCODING *BORDATELLA BRONCHISEPTICA* FIMBRIAL PROTEINS (FIMN), VECTORS, AND EXPRESSION SYSTEMS THEREFOR**

(75) Inventors: David A. Bemis, Maryville, TN (US); Stephen A. Kania, Powell, TN (US); Robert N. Moore, Knoxville, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/570,214

(22) Filed: May 12, 2000

Related U.S. Application Data

(60) Provisional application No. 60/134,181, filed on May 14, 1999.

(51) Int. Cl.$^7$ ........................ C12P 21/06; C12N 15/00; C12N 1/20; C07H 21/04

(52) U.S. Cl. .................... 435/69.1; 435/69.7; 435/70.1; 435/71.1; 435/320.1; 435/325; 435/252.3; 435/254.11; 435/257.3; 530/350; 536/23.4; 536/23.7; 536/24.32; 536/24.33; 935/11; 935/12; 935/22; 935/66

(58) Field of Search ............................ 536/23.7, 24.32, 536/24.33, 24.3, 23.4; 530/300, 350, 820, 825; 435/69.1, 69.7, 70.1, 71.1, 320.1, 325, 252.3, 254.11, 257.3; 935/11, 12, 22, 66

(56) References Cited

U.S. PATENT DOCUMENTS 5,939,064 A * 8/1999 Savelkoul et al.

OTHER PUBLICATIONS

Sambrouk et al, in "Molecular Cloning A Labortory Manual", pp. 17.2–17.43 Cold Spring Harbor Press Inc., 1989.*
Gerhold et al, BioEssays. 18(12):973–981, 1996.*
Wells et al, J. of Leukayte Biology 61(5):545–550, 1997.*
Russell et al, Journal of Molecular Biology 244:332–350, 1994.*
Rudinger, in "Pepticle Hormones" ed. Parsons, J.A., University Park Press, pp. 1–6, Jun. 1976.*
Burgess et al, The Journal of Cell Biology, 111:2129–2138, 1990.*
Lazar et al, Molecular and Cellular Biology, 8(3):1247–1252, 1988.*
Jobling et al, Mol. Microbiol, 5(7):1755–67, 1991.*
Boehnager Mannheim Biochemsitry, 1991 catalog. p. 557, 1991.*
Stratagene, 1991 Product Catalog, p. 66, 1991.*
Gibcobiol., Catalogue & Reference Guide 1992 p. 292.*
Pronega (1993/1994 Catalog) pp. 90–91.*
New England Biolabs Catalog, 1986/1987 pp. 60–62.*

Kania, S.A., et al. [2000] "Characterization of fimN, a new *Bordetella bronchiseptica* major fimbrial subunit gene," *Gene* 256:149–55.
Altschul, Stephen F., Warren Gish, Webb Miller, Eugene W. Myers, David J. Lipman (1990) "Basic Local Alignment Search Tool" *J. Mol. Biol.* 215(403–410.

Boschwitz, Jeffrey S., Han G. J. van Der Heide, Frits R. Mooi, David A. Relman (1997) "*Bordetella bronchiseptica* Expresses the Fimbrial Structural Subunit Gene fimA" *Journal of Bacteriology* 179(24):78827885.

Burns, Jr., Eugene H., John M. Norman, Monty D. Hatcher, David A. Bemis (1993) "Fimbriae and Determination of Host Species Specificity of *Bordetella bronchiseptica*" *Journal of Clinical Microbiology* 31(7):1838–1844.

Cox, Graham J. M., Tim J. Zamb, Lorne A. Babiuk (1993) "Bovine Herpesvirus 1: Immune Responses in Mice and Cattle Injected with Plasmid DNA" *Journal of Virology* 67(9):5664–5667.

Meade, Harry M., Sharon R. Long, Gary B. Ruvkun, Susan E. Brown, Fred M. Ausubel (1982) "Physical and Genetic characterization of Symbiotic and Auxotrophic Mutants of *Rhizobium meliloti* Induced by Transposon Tn5 Mutagenesis" *Journal of Bacteriology* 149:114–122.

Mooi, Frits R., Wim H. Jansen, Henk Brunings, Henk Gielen, Han G. J. van der Heide, Henk C. Walvoort and Piet A.M. Guinee (1992) "Construction and analysis of *Bordetella pertussis* mutants defective in the production of fimbriae" *Microbiol Pathogenesis* 12:127–135.

Riboli, B. P. Pedroni, A. Cuzzoni, G. Grandi and F. de Ferra (1991) "Expression of *Bordetella pertussis* fimbrial (fim) genes in *Bordetella bronchiseptica*: fimX is expressed at a low level and vir–regulated" *Microbial Pathogenesis* 10:393–403.

Sedegah, Martha, Richard Hedstrom, Peter Hobart, and Stephen L. Hoffman (1994) "Protection against malaria by immunization with plasmid DNA encoding circumsporozoite protein" *Proc Natl. Acad. Sci. USA* 91:9866–9870.

Weiss, Alison A., Stanley Falkow (1982) "Plasmid Transfer to *Bordetella Pertussis*: Conjugation and Transformation" *Journal of Bacteriology* 152(1):549–552.

Willems, Rob, Annet Paul, Han G.J. vn der Heide, Anja R.ter Avest and Frits R. Mooi (1990) "Fimbrial phase variation in *Bordetella pertussis*: a novel mechanism for transcriptional regulation" *The EMBO Journal* 9(9):2803–2809.

F. Schödel, M.–T. Aguado and P.–H. Lambert (1994) Special Conference "Introduction: Nucleic Acid Vaccines, WHO, Geneva, May 17–18, 1994" *Vaccine* 12:1491.

* cited by examiner

*Primary Examiner*—Patricia A. Duffy
(74) *Attorney, Agent, or Firm*—Saliwanchik, Lloyd & Saliwanchik

(57) ABSTRACT

In one aspect, the subject invention concerns the cloning and characterization of a previously unidentified gene, provisionally named fim N, encoding a fimbrial protein that is putatively involved in the attachment of *B. bronchiseptica* to respiratory epithelium. This gene has been subcloned into a bacterial expression vector, and the recombinant protein has been isolated and partially characterized.

15 Claims, 7 Drawing Sheets

```
            1                                                         50
fim2dna     CCCCCCCCCC CCCCCCCCTA AGACCTAAGA TCGTGGCTCC \TAACTCTTC
fimndna          CCCCCC CCCCCGGCGA ACTCTAATAT TCTTGCTTCC TCCGTAATTC
fim3dna     CCCCCCCCC  CCCCCCCCCC GGACCTAATA TTCTGATGCC GACGCCAAGC 51                                                        100
fim2dna     TGGCGCCAAG ACGCCCGTGT TACC..CATG CAAGTCCCTT TCCAACGCGC
fimndna     CGGCGCGCTT GCGCCAATAC CAGCATGAAG CACTTT.GCC GCCACCGTGG
fim3dna     ACATGACGGC ACCCCTCAGT CTCAGAATCA CCATCTCCAA GTTTTCATAC 101                                                       150
fim2dna     CCTGCC..GC TGTGCTTGCG GGCCGCTCTG GCGGCCATTG CGTCCGCGGC
fimndna     GCTGGC..GC TGGCCTGCCT GGCCAGCGCA TTGGGCCTGC ACACCGCCGT
fim3dna     CCCGCCTTGC GCACCGCGCT TATCCTTGCC GCCTCGCCCG TGCTGCCGGC 151                                                       200
fim2dna     GCACGCCGAC GACGGCACCA TCGTCATCAC CGGCACCATC ACCGACACCA
fimndna     CCATGCCAAC GACGGCACGA TCGTGATCAC CGGCAACATC GTCGACAACA
fim3dna     GCATGCCAAC GACGGCACCA TCGTCATCAC CGGCAGCATC TCCGACCAGA 201                                                       250
fim2dna     CCTGCGTCAT CGAGGACCCG GCCGGCCCCA CGCACACCAA GGTGGTGCAA
fimndna     CCTGCGAGGT CGTGGATCCG CCGCAGCCCA ATCACATCAA GGTGGTGCAT
fim3dna     CCTGCGTCAT CGAAGAGCCC AGCGCCCCCA ACCATATCAA GGTCGTGCAA 251                                                       300
fim2dna     TTGCCCAAGA TATCCAAGAG CGCGCTGGCC AAGGATGGAG ACGAAGCTGG
fimndna     CTGCCCAAGA TCTCGACAAG CGCGCTCAAG AAGACCGGCG ATACCGCCGG
fim3dna     CTGCCCAAGA TTTCCAAGAA CGCGCTCAGG AACGACGGCG ACACCGCCGG 301                                                       350
fim2dna     CCGTACGCCC TTCCTGATCA CGCTCAAGGA CTGCCCCTCG TCCCTGAACA
fimndna     CGCGACGCCG TTTTCCATCA AGCTGCAGAA CTGCCCCGAA TCGCTGGGCA
fim3dna     CGCCACGCCC TTCGACATCA GGCTGAAGGA ATGCCCC... ...CAGCTGG 351                                                       400
fim2dna     ATGGCGTGAA AGCGTACTTC GAGCCTGGGC CGACCACCGA CTACGCTACC
fimndna     ATGGCGTGAA GCTGTACTTC GAGCCCGGTC CGACCACCGA CTACAGCACC
fim3dna     GCGCGCTCAA GCTGTATTTC GAGCCCGGCA TCACCACCAA CTACGACACC 401                                                       450
fim2dna     GGCGACCTAA AGGCGTATTC GATCGCCTAC AACAACAACC CCGCCACCAC
fimndna     AGGGACCTGA CCGCCTACAA GCTGGCCTAC ACCGCCAACA GCACGACCAA
fim3dna     GGCGATCTGA TCGCCTACAA GCAGGCCTAC AACGCATCCG GCAACGGCAA 451                                                       500
fim2dna     CCAAAATGCG ATCATCGCTG CAAGCGAAGC GCAGGGCGTG CAAATCCGCA
fimndna     CAGCAA...C ATTGTTGCCG GCCAGGTCGC GGAAGGAGTG CAGATCCGTA
fim3dna     CCTGAGCACC GTGTCGTCCG CCACCAAGGC CAAGGGCGTG GAATTCCGCC 501                                                       550
fim2dna     TCTCCAACCA GAACGGCACC AAGATCCCCA TGGGCGTGGA CGCCGCCGCC
fimndna     TCGCCAACCT GGATGGCACC CAGATTCCCA TGGGCGAAAA CGCCGCGGGC
fim3dna     TGGCCAACCT CAACGGCCAG CACATCCGCA TGGGCACCGA CGAAACCACG 551                                                       600
fim2dna     CAGAACGCCC AGGCCTTC.. .AACCCCGTC ACCGACACCG CCGACAACGC
fimndna     CAGAATGCGC GCGGCTTC.. .GATCCGGTC GCGCAAACCG GCAACAGGG
fim3dna     CAAGCCGCGC AAACCTTCAC GGGCACTGAT GTCACCAACG GCGGCAACAC 601                                                       650
fim2dna     CAAGAAGAAG GTCACGTTGC GCTACCTGGC ATCGTACGTA AAGAAATCC.
fimndna     CAAGAAGGAA GTCACCTTGC GCTATCTGGC CGCCTATGTG AAGAAAGCCA
fim3dna     CACCAAAAGC TATACCCTGC GCTATCTCGC CTCGTACGTG AAGAAACCCA 651                                                       700
fim2dna     ..GGCAACAT TACTGCCGGG CAACTCACGA CATACGTCGG TTTTTCCATG
fimndna     CAGGCACAAT TTCTGCAAGC GCGATAACCA CTTACGTNAG CTTTTCGGTC
fim3dna     ACGAAGATGT CGACGCGGCG CAGATGACCA GCTACGTCGG CTTTTCCGTC 701                                                       750
fim2dna     ATCTATCCGT AA..CCCCGA CTCCTGCCCT CCAGGCAGGC CAAGCGGGCT
fimndna     ATCTATCCTT AG..ATATGA GGCCNGGGCT TGATAAGGAT AATCTACACA
fim3dna     GTCTATCCCT GAGTTCTCGC GCCATCCAAA AAAACCGGC AAGCCTTGCG
```

FIG. 1

```
             1                                                                    50
fim2      MQVPFQRAL  PLCLRAALAA  IASAAHADDG  TIVITGTITD  TTCVIEDPAG
fimn      MKHFRRHRGL ALACLASALG  LHTAVHANDG  TIVITGNIVD  NTCEVVDPPQ
fimx            MQAK TFLLGAALAG  VALAAHAEDG  TIVITGTITD  QTCTIEDP.S
fim3      MSKFSYPA   LRTALILAAS  PVLPAHANDG  TIVITGSISD  QTCVIEEPSA
fima      MNLKFAGI   ALGLTACALT  YQHQVFAADG  TLVITGAITD  TTCKINGAEP 51                                                                   100
fim2      PTHTKVVQLP KISKSALAKD  GDEAGRTPFL  ITLKDCPSSL  NN.GVKAYFE
fimn      PNHIKVVHLP KISTSALKKT  GDTAGATPFS  IKLQNCPESL  GN.GVKLYFE
fimx      PGYIKVVHLP TISKSALKNA  GDVAGRTRFD  IKLKDCPTTV  .N.TLKLYFE
fim3      PNHIKVVQLP KISKNALRND  GDTAGATPFD  IRLKECPQL.  .G.ALKLYFE
fima      PTNI.AVQLP TISRTALKDV  GSTAGGTVFD  VKLTECPQAL  NGQQVGLFFE 101                                                                  150
fim2      PGPTTDYATG DLKAYSIAYN  NNPATTQNAI  IAASEAQGVQ  IRISNQNGTK
fimn      PGPTTDYSTR DLTAYKLAYT  AN.STTNSNI  VAGQVAEGVQ  IRIANLDGTQ
fimx      PGPTTDYGTK DLKAYKQAWY  VDAATLLKSP  PSVTEAKGVQ  IRLMNLNGKQ
fim3      PGITTNYDTG DLIAYKQAYN  ASGNGNLSTV  SSATKAKGVE  FRLANLNGQH
fima      PGGTVDYTSG NLFAYR....  ..ADSQGVEQ  VPQTKADNVQ  FQLANLDGSA 151                                                                  200
fim2      IPMGVDAAAQ NAQAFNPVTD  T.ADNAKKKV  TLRYLASYVK  K.SGNITAGQ
fimn      IPMGENAAGQ NARGFDPVAQ  T.GQQGKKEV  TLRYLAAYVK  KATGTISASA
fimx      IPMGETEPNQ HAAAFSGTMQ  A.G.QAKKSF  TLHYLAGYVK  KASGEVEATM
fim3      IRMGTDETTQ AAQTFTGTDV  TNGGNTTKSY  TLRYLASYVK  KPNEDVDAAQ
fima      IHLGRNKGAQ AAQTF..LVS  QTAGSSTYGT  TLRYLARYIR  SGAGSIVAGN 201        212
fim2      LTTYVGFSMI  YP
fimn      ITTYVSFSVI  YP
fimx      LTTYVGFSVV  YP
fim3      MTSYVGFSVV  YP
fima      LRSQVGFSVM  YP
```

```
  1 ATGAAGCACTTTCGCCGCCACCGTGGGCTGGCTGGCCTGGCCAGGCATTGGGC  60
    M  K  H  F  R  R  H  R  G  L  A  L  A  C  L  A  S  A  L  G
 61 CTGCACACCGCCCGTCCATGCCAACGGACGATCGTGATCACCGGCAACATCGTCGAC 120
    L  H  T  A  V  H  A  N  D  G  T  I  V  I  T  G  N  I  V  D
121 AACACCTGCGAGGTCGTGGATCCGCAGCCCAATCACATCAAGGTGGTGCATCTGCCC 180
    N  T  C  E  V  V  D  P  P  Q  P  N  H  I  K  V  V  H  L  P
181 AAGATCTGACAAGCGCTCAAGAAGACCGGCGATACCGGCGCCGGCGACGCCGTTTTCC 240
    K  I  S  T  S  A  L  K  K  T  G  D  T  A  G  A  T  P  F  S
241 ATCAAGCTGCAGAACTGCCCCGAATCGCTGGGCAATGGCGTGAAGCTGTACTTCGAGCCC 300
    I  K  L  Q  N  C  P  E  S  L  G  N  G  V  K  L  Y  F  E  P
301 GGTCCGACCACCGACTACAGCACCAGGGACCTGACCGCCTACAAGCTGGCCTACACCGCC 360
    G  P  T  T  D  Y  S  T  R  D  L  T  A  Y  K  L  A  Y  T  A
361 AACAGCACGACCAACAGCAACATTGTTGCCGGCCAGTGCGGAAGGAGTGCAGATCCGT 420
    N  S  T  T  N  S  N  I  V  A  G  Q  V  A  E  G  V  Q  I  R
421 ATCGCCAACCTGGATGGCACCCAGATTCCCATGGGCGAATACGCCCAGAATGCG 480
    I  A  N  L  D  G  T  Q  I  P  M  G  E  N  A  A  G  Q  N  A
481 CGCGGCTTCGATCCGGTCGCGCAAACCGGGCAACAGGGCAAGAAGGAAGTCACCTTGCGC 540
    R  G  F  D  P  V  A  Q  T  G  Q  Q  G  K  K  E  V  T  L  R
541 TATCTGGCCGCCTATGTGAAGAAAGCCACAGGCACAATTTCTGCAAGCGCGATAACCACT 600
    Y  L  A  A  Y  V  K  K  A  T  G  T  I  S  A  S  A  I  T  T
601 TACGTAGGCTTTTCGGTCATCTATCCTTAGA 631
    Y  V  G  F  S  V  I  Y  P  *
```

FIG. 4

| Fimbrial Protein | Predicted Protein | | Predicted Protein Minus Signal Sequence | |
|---|---|---|---|---|
| | % Similarity | % Identity | % Similarity | % Identity |
| B.pertussis fim2 | 65.0 | 60.7 | 70.0 | 65.5 |
| B.bronchiseptica fim2 | 62.3 | 59.4 | 66.8 | 64.0 |
| B.pertussis fimX | 59.0 | 55.5 | 63.1 | 59.2 |
| B.bronchiseptica fim3 | 58.0 | 52.2 | 60.5 | 55.0 |
| B.pertussis fim3 | 57.9 | 53.3 | 61.3 | 56.8 |
| B.bronchiseptica fimX | 51.0 | 44.0 | 52.6 | 45.7 |

FIG. 5

|   |   | A | | B |
|---|---|---|---|---|
| BB FimN pBS84 | GGGTTCCTACATATCTATCAGCCCCCCCCGGCGAACTCTAATATTCT |
| BB FimN 110H | GGGTTCCTACATATCTATCAGCCCCCCCCCGGCGAACTCTAATATTCT |
| BP Fim2 | TGTTTCCCACATCGGAATCAGCCCCCCCCCCCTAAGACCTAAGAT |
| BP FimX | AAATTCCTACACATCCATCAGCCCCCCCCCCGAGGCGTCTAAT |
| BP Fim3 | AAATTCCCACACCAACCATCAGCCCCCCCCCCGGACCTGATATTCT |
| BB Fim2 | TGTTTCCCACATCGGAATCAGCCCCCCCCCCCTAAGACCTAAGAT |
| BB Fim3 | AAATTCCCACACAACCATCAGCCCCCCCCCCGGACCTAATATTCT |
| BB FimX | AATTCCTAGATACCCATGAGGCCCCCCCCCCCTGAGGCGTCCAATAATCT |

FIG. 6

| Strain | Bvg Phenotype | Attached Bacteria |
|---|---|---|
| 110H | + | 995± 132 |
| 110NH | - | 186± 88 |
| R-5 | + | 544± 21 |
| R-5 pLAFR1 | + | 589± 97 |
| R-5 pGB710 | + | 1268± 40 |

FIG. 7

SEQUENCE LISTING

```
<160> NUMBER OF SEQ ID NOS: 21

<210> SEQ ID NO 1
<211> LENGTH: 27
<212> TYPE: DNA
<213> ORGANISM: Bordetella bronchiseptica

<400> SEQUENCE: 1
ggaagcttgc catcaccaac ttatgtg                                            27

<210> SEQ ID NO 2
<211> LENGTH: 27
<212> TYPE: DNA
<213> ORGANISM: Bordetella bronchiseptica

<400> SEQUENCE: 2
gggaattcga ttatccttat caagccc                                            27

<210> SEQ ID NO 3
<211> LENGTH: 631
<212> TYPE: DNA
<213> ORGANISM: Bordetella bronchiseptica
<220> FEATURE:
<221> NAME/KEY: CDS
<222> LOCATION: (1)..(630)
<223> OTHER INFORMATION:

<400> SEQUENCE: 3 atg aag cac ttt cgc cgc cac cgt ggg ctg gcg ctg gcc tgc ctg gcc        48
Met Lys His Phe Arg Arg His Arg Gly Leu Ala Leu Ala Cys Leu Ala
1               5                   10                  15 agc gca ttg ggc ctg cac acc gcc gtc cat gcc aac gac ggc acg atc        96
Ser Ala Leu Gly Leu His Thr Ala Val His Ala Asn Asp Gly Thr Ile
            20                  25                  30 gtg atc acc ggc aac atc gtc gac aac acc tgc gag gtc gtg gat ccg       144
Val Ile Thr Gly Asn Ile Val Asp Asn Thr Cys Glu Val Val Asp Pro
        35                  40                  45 ccg cag ccc aat cac atc aag gtg gtg cat ctg ccc aag atc tcg aca       192
Pro Gln Pro Asn His Ile Lys Val Val His Leu Pro Lys Ile Ser Thr
    50                  55                  60 agc gcg ctc aag aag acc ggc gat acc gcc ggc gcg acg ccg ttt tcc       240
Ser Ala Leu Lys Lys Thr Gly Asp Thr Ala Gly Ala Thr Pro Phe Ser
65                  70                  75                  80 atc aag ctg cag aac tgc ccc gaa tcg ctg ggc aat ggc gtg aag ctg       288
Ile Lys Leu Gln Asn Cys Pro Glu Ser Leu Gly Asn Gly Val Lys Leu
                85                  90                  95 tac ttc gag ccc ggt ccg acc acc gac tac agc acc agg gac ctg acc       336
Tyr Phe Glu Pro Gly Pro Thr Thr Asp Tyr Ser Thr Arg Asp Leu Thr
            100                 105                 110 gcc tac aag ctg gcc tac acc gcc aac agc acg acc aac agc aac att       384
Ala Tyr Lys Leu Ala Tyr Thr Ala Asn Ser Thr Thr Asn Ser Asn Ile
        115                 120                 125
```

```
gtt gcc ggc cag gtc gcg gaa gga gtg cag atc cgt atc gcc aac ctg    432
Val Ala Gly Gln Val Ala Glu Gly Val Gln Ile Arg Ile Ala Asn Leu
    130                 135                 140 gat ggc acc cag att ccc atg ggc gaa aac gcc gcg ggc cag aat gcg    480
Asp Gly Thr Gln Ile Pro Met Gly Glu Asn Ala Ala Gly Gln Asn Ala
145                 150                 155                 160 cgc ggc ttc gat ccg gtc gcg caa acc ggg caa cag ggc aag aag gaa    528
Arg Gly Phe Asp Pro Val Ala Gln Thr Gly Gln Gln Gly Lys Lys Glu
                165                 170                 175 gtc acc ttg cgc tat ctg gcc gcc tat gtg aag aaa gcc aca ggc aca    576
Val Thr Leu Arg Tyr Leu Ala Ala Tyr Val Lys Lys Ala Thr Gly Thr
            180                 185                 190 att tct gca agc gcg ata acc act tac gta ggc ttt tcg gtc atc tat    624
Ile Ser Ala Ser Ala Ile Thr Thr Tyr Val Gly Phe Ser Val Ile Tyr
        195                 200                 205 cct tag a                                                          631
Pro
```

<210> SEQ ID NO 4
<211> LENGTH: 209
<212> TYPE: PRT
<213> ORGANISM: Bordetella bronchiseptica

<400> SEQUENCE: 4

```
Met Lys His Phe Arg Arg His Arg Gly Leu Ala Leu Ala Cys Leu Ala
1               5                   10                  15

Ser Ala Leu Gly Leu His Thr Ala Val His Ala Asn Asp Gly Thr Ile
                20                  25                  30

Val Ile Thr Gly Asn Ile Val Asp Asn Thr Cys Glu Val Val Asp Pro
            35                  40                  45

Pro Gln Pro Asn His Ile Lys Val Val His Leu Pro Lys Ile Ser Thr
        50                  55                  60

Ser Ala Leu Lys Lys Thr Gly Asp Thr Ala Gly Ala Thr Pro Phe Ser
65                  70                  75                  80

Ile Lys Leu Gln Asn Cys Pro Glu Ser Leu Gly Asn Gly Val Lys Leu
                85                  90                  95

Tyr Phe Glu Pro Gly Pro Thr Thr Asp Tyr Ser Thr Arg Asp Leu Thr
            100                 105                 110

Ala Tyr Lys Leu Ala Tyr Thr Ala Asn Ser Thr Thr Asn Ser Asn Ile
        115                 120                 125

Val Ala Gly Gln Val Ala Glu Gly Val Gln Ile Arg Ile Ala Asn Leu
130                 135                 140

Asp Gly Thr Gln Ile Pro Met Gly Glu Asn Ala Ala Gly Gln Asn Ala
145                 150                 155                 160

Arg Gly Phe Asp Pro Val Ala Gln Thr Gly Gln Gln Gly Lys Lys Glu
                165                 170                 175

Val Thr Leu Arg Tyr Leu Ala Ala Tyr Val Lys Lys Ala Thr Gly Thr
            180                 185                 190

Ile Ser Ala Ser Ala Ile Thr Thr Tyr Val Gly Phe Ser Val Ile Tyr
        195                 200                 205

Pro
```

<210> SEQ ID NO 5
<211> LENGTH: 736
<212> TYPE: DNA
<213> ORGANISM: Bordetella bronchiseptica
<220> FEATURE:

```
<221> NAME/KEY: misc_feature
<222> LOCATION: (1)..(736)
<223> OTHER INFORMATION: n is a, g, c, t, or u

<400> SEQUENCE: 5
cccccccccc cggcgaactc taatattctt gcttcctccg taattccggc gcgcttgcgc     60
caataccagc atgaagcact tcgccgcca ccgtgggctg gcgctggcct gcctggccag     120
cgcattgggc ctgcacaccg ccgtccatgc caacgacggc acgatcgtga tcaccggcaa    180
catcgtcgac aacacctgcg aggtcgtgga tccgccgcag cccaatcaca tcaaggtggt    240
gcatctgccc aagatctcga aagcgcgct caagaagacc ggcgataccg ccggcgcgac     300
gccgttttcc atcaagctgc agaactgccc cgaatcgctg gcaatggcg tgaagctgta    360 cttcgagccc ggtccgacca ccgactacag caccagggac ctgaccgcct acaagctggc    420
ctacaccgcc aacagcacga ccaacagcaa cattgttgcc ggccaggtcg cggaaggagt    480
gcagatccgt atcgccaacc tggatggcac ccagattccc atgggcgaaa acgccgcggg   540
ccagaatgcg cgcggcttcg atccggtcgc gcaaaccggg caacagggca agaaggaagt   600
caccttgcgc tatctggccg cctatgtgaa gaaagccaca ggcacaattt ctgcaagcgc   660
gataaccact tacgtaggct tttcggtcat ctatccttag atatgaggcc ngggcttgat    720
aaggataatc tacaca                                                    736

<210> SEQ ID NO 6
<211> LENGTH: 743
<212> TYPE: DNA
<213> ORGANISM: Bordetella bronchiseptica - Fim 3
<220> FEATURE:
<221> NAME/KEY: CDS
<222> LOCATION: (82)..(705)
<223> OTHER INFORMATION:

<400> SEQUENCE: 6
cccccccccc cccccccccg gacctaatat tctgatgccg acgccaagca catgacggca     60
cccctcagtc tcagaatcac c atg tcc aag ttt tca tac ccc gcc ttg cgc      111
                         Met Ser Lys Phe Ser Tyr Pro Ala Leu Arg
                          1               5                  10 acc gcg ctt atc ctt gcc gcc tcg ccc gtg ctg ccg gcg cat gcc aac      159
Thr Ala Leu Ile Leu Ala Ala Ser Pro Val Leu Pro Ala His Ala Asn
              15                  20                  25 gac ggc acc atc gtc atc acc ggc agc atc tcc gac cag acc tgc gtc      207
Asp Gly Thr Ile Val Ile Thr Gly Ser Ile Ser Asp Gln Thr Cys Val
         30                  35                  40 atc gaa gag ccc agc gcc ccc aac cat atc aag gtc gtg caa ctg ccc      255
Ile Glu Glu Pro Ser Ala Pro Asn His Ile Lys Val Val Gln Leu Pro
     45                  50                  55 aag att tcc aag aac gcg ctc agg aac gac ggc gac acc gcc ggc gcc      303
Lys Ile Ser Lys Asn Ala Leu Arg Asn Asp Gly Asp Thr Ala Gly Ala
 60                  65                  70 acg ccc ttc gac atc agg ctg aag gaa tgc ccc cag ctg ggc gcg ctc      351
Thr Pro Phe Asp Ile Arg Leu Lys Glu Cys Pro Gln Leu Gly Ala Leu
 75                  80                  85                  90 aag ctg tat ttc gag ccc ggc atc acc acc aac tac gac acc ggc gat      399
Lys Leu Tyr Phe Glu Pro Gly Ile Thr Thr Asn Tyr Asp Thr Gly Asp
                 95                 100                 105 ctg atc gcc tac aag cag gcc tac aac gca tcc ggc aac ggc aac ctg      447
Leu Ile Ala Tyr Lys Gln Ala Tyr Asn Ala Ser Gly Asn Gly Asn Leu
             110                 115                 120 agc acc gtg tcg tcc gcc acc aag gcc aag ggc gtg gaa ttc cgc ctg      495
```

-continued

```
Ser Thr Val Ser Ser Ala Thr Lys Ala Lys Gly Val Glu Phe Arg Leu
        125                 130                 135 gcc aac ctc aac ggc cag cac atc cgc atg ggc acc gac gaa acc acg    543
Ala Asn Leu Asn Gly Gln His Ile Arg Met Gly Thr Asp Glu Thr Thr
    140                 145                 150 caa gcc gcg caa acc ttc acg ggc act gat gtc acc aac ggc ggc aac    591
Gln Ala Ala Gln Thr Phe Thr Gly Thr Asp Val Thr Asn Gly Gly Asn
155                 160                 165                 170 acc acc aaa agc tat acc ctg cgc tat ctc gcc tcg tac gtg aag aaa    639
Thr Thr Lys Ser Tyr Thr Leu Arg Tyr Leu Ala Ser Tyr Val Lys Lys
                175                 180                 185 ccc aac gaa gat gtc gac gcg gcg cag atg acc agc tac gtc ggc ttt    687
Pro Asn Glu Asp Val Asp Ala Ala Gln Met Thr Ser Tyr Val Gly Phe
            190                 195                 200 tcc gtc gtc tat ccc tga gttctcgcgc catccaaaaa aaaccggcaa gccttgcg  743
Ser Val Val Tyr Pro
        205
```

<210> SEQ ID NO 7
<211> LENGTH: 207
<212> TYPE: PRT
<213> ORGANISM: Bordetella bronchiseptica - Fim 3

<400> SEQUENCE: 7

```
Met Ser Lys Phe Ser Tyr Pro Ala Leu Arg Thr Ala Leu Ile Leu Ala
1               5                   10                  15

Ala Ser Pro Val Leu Pro Ala His Ala Asn Asp Gly Thr Ile Val Ile
                20                  25                  30

Thr Gly Ser Ile Ser Asp Gln Thr Cys Val Ile Glu Glu Pro Ser Ala
            35                  40                  45

Pro Asn His Ile Lys Val Val Gln Leu Pro Lys Ile Ser Lys Asn Ala
        50                  55                  60

Leu Arg Asn Asp Gly Asp Thr Ala Gly Ala Thr Pro Phe Asp Ile Arg
65                  70                  75                  80

Leu Lys Glu Cys Pro Gln Leu Gly Ala Leu Lys Leu Tyr Phe Glu Pro
                85                  90                  95

Gly Ile Thr Thr Asn Tyr Asp Thr Gly Asp Leu Ile Ala Tyr Lys Gln
                100                 105                 110

Ala Tyr Asn Ala Ser Gly Asn Gly Asn Leu Ser Thr Val Ser Ser Ala
            115                 120                 125

Thr Lys Ala Lys Gly Val Glu Phe Arg Leu Ala Asn Leu Asn Gly Gln
        130                 135                 140

His Ile Arg Met Gly Thr Asp Glu Thr Thr Gln Ala Ala Gln Thr Phe
145                 150                 155                 160

Thr Gly Thr Asp Val Thr Asn Gly Gly Asn Thr Thr Lys Ser Tyr Thr
                165                 170                 175

Leu Arg Tyr Leu Ala Ser Tyr Val Lys Lys Pro Asn Glu Asp Val Asp
                180                 185                 190

Ala Ala Gln Met Thr Ser Tyr Val Gly Phe Ser Val Val Tyr Pro
            195                 200                 205
```

<210> SEQ ID NO 8
<211> LENGTH: 738
<212> TYPE: DNA
<213> ORGANISM: Bordetella bronchiseptica - Fim 2
<220> FEATURE:
<221> NAME/KEY: CDS
<222> LOCATION: (76)..(702)
<223> OTHER INFORMATION:

<400> SEQUENCE: 8

```
cccccccccc cccccccccta agacctaaga tcgtggctcc ataactcttc tggcgccaag      60
acgcccgtgt taccc atg caa gtc cct ttc caa cgc gcc ctg ccg ctg tgc       111
                 Met Gln Val Pro Phe Gln Arg Ala Leu Pro Leu Cys
                 1               5                   10 ttg cgg gcc gct ctg gcg gcc att gcg tcc gcg gcg cac gcc gac gac        159
Leu Arg Ala Ala Leu Ala Ala Ile Ala Ser Ala Ala His Ala Asp Asp
        15                  20                  25 ggc acc atc gtc atc acc ggc acc atc acc gac acc acc tgc gtc atc        207
Gly Thr Ile Val Ile Thr Gly Thr Ile Thr Asp Thr Thr Cys Val Ile
    30                  35                  40 gag gac ccg gcc ggc ccc acg cac acc aag gtg gtg caa ttg ccc aag        255
Glu Asp Pro Ala Gly Pro Thr His Thr Lys Val Val Gln Leu Pro Lys
45                  50                  55                  60 ata tcc aag agc gcg ctg gcc aag gat gga gac gaa gct ggc cgt acg        303
Ile Ser Lys Ser Ala Leu Ala Lys Asp Gly Asp Glu Ala Gly Arg Thr
                65                  70                  75 ccc ttc ctg atc acg ctc aag gac tgc ccc tcg tcc ctg aac aat ggc        351
Pro Phe Leu Ile Thr Leu Lys Asp Cys Pro Ser Ser Leu Asn Asn Gly
            80                  85                  90 gtg aaa gcg tac ttc gag cct ggg ccg acc acc gac tac gct acc ggc        399
Val Lys Ala Tyr Phe Glu Pro Gly Pro Thr Thr Asp Tyr Ala Thr Gly
        95                  100                 105 gac cta aag gcg tat tcg atc gcc tac aac aac aac ccc gcc acc acc        447
Asp Leu Lys Ala Tyr Ser Ile Ala Tyr Asn Asn Asn Pro Ala Thr Thr
    110                 115                 120 caa aat gcg atc atc gct gca agc gaa gcg cag ggc gtg caa atc cgc        495
Gln Asn Ala Ile Ile Ala Ala Ser Glu Ala Gln Gly Val Gln Ile Arg
125                 130                 135                 140 atc tcc aac cag aac ggc acc aag atc ccc atg ggc gtg gac gcc gcc        543
Ile Ser Asn Gln Asn Gly Thr Lys Ile Pro Met Gly Val Asp Ala Ala
                145                 150                 155 gcc cag aac gcc cag gcc ttc aac ccc gtc acc gac acc gcc gac aac        591
Ala Gln Asn Ala Gln Ala Phe Asn Pro Val Thr Asp Thr Ala Asp Asn
            160                 165                 170 gcc aag aag aag gtc acg ttg cgc tac ctg gca tcg tac gta aag aaa        639
Ala Lys Lys Lys Val Thr Leu Arg Tyr Leu Ala Ser Tyr Val Lys Lys
        175                 180                 185 tcc ggc aac att act gcc ggg caa ctc acg aca tac gtc ggt ttt tcc        687
Ser Gly Asn Ile Thr Ala Gly Gln Leu Thr Thr Tyr Val Gly Phe Ser
    190                 195                 200 atg atc tat ccg taa ccccgactcc tgccctccag gcaggccaag cgggct           738
Met Ile Tyr Pro
205
```

<210> SEQ ID NO 9
<211> LENGTH: 208
<212> TYPE: PRT
<213> ORGANISM: Bordetella bronchiseptica - Fim 2

<400> SEQUENCE: 9

```
Met Gln Val Pro Phe Gln Arg Ala Leu Pro Leu Cys Leu Arg Ala Ala
1               5                   10                  15

Leu Ala Ala Ile Ala Ser Ala Ala His Ala Asp Asp Gly Thr Ile Val
            20                  25                  30

Ile Thr Gly Thr Ile Thr Asp Thr Thr Cys Val Ile Glu Asp Pro Ala
        35                  40                  45

Gly Pro Thr His Thr Lys Val Val Gln Leu Pro Lys Ile Ser Lys Ser
```

```
                     50                  55                  60
Ala Leu Ala Lys Asp Gly Asp Glu Ala Gly Arg Thr Pro Phe Leu Ile
 65                  70                  75                  80

Thr Leu Lys Asp Cys Pro Ser Ser Leu Asn Asn Gly Val Lys Ala Tyr
                 85                  90                  95

Phe Glu Pro Gly Pro Thr Thr Asp Tyr Ala Thr Gly Asp Leu Lys Ala
            100                 105                 110

Tyr Ser Ile Ala Tyr Asn Asn Pro Ala Thr Thr Gln Asn Ala Ile
        115                 120                 125

Ile Ala Ala Ser Glu Ala Gln Gly Val Gln Ile Arg Ile Ser Asn Gln
    130                 135                 140

Asn Gly Thr Lys Ile Pro Met Gly Val Asp Ala Ala Gln Asn Ala
145                 150                 155                 160

Gln Ala Phe Asn Pro Val Thr Asp Thr Ala Asp Asn Ala Lys Lys Lys
                165                 170                 175

Val Thr Leu Arg Tyr Leu Ala Ser Tyr Val Lys Lys Ser Gly Asn Ile
            180                 185                 190

Thr Ala Gly Gln Leu Thr Thr Tyr Val Gly Phe Ser Met Ile Tyr Pro
        195                 200                 205
```

<210> SEQ ID NO 10
<211> LENGTH: 845
<212> TYPE: DNA
<213> ORGANISM: Bordetella bronchiseptica - Fim x
<220> FEATURE:
<221> NAME/KEY: CDS
<222> LOCATION: (25)..(627)
<223> OTHER INFORMATION:

<400> SEQUENCE: 10

```
gatcccttct ttactccagc ctgt atg caa gcc aaa acg ttc ctc ctg ggc        51
                         Met Gln Ala Lys Thr Phe Leu Leu Gly
                           1               5 gcg gcg ctc gcc ggc gtc gcg ctc gcc gcc cat gcc gaa gac ggc acc       99
Ala Ala Leu Ala Gly Val Ala Leu Ala Ala His Ala Glu Asp Gly Thr
 10                  15                  20                  25 att gtc att acc ggc acg atc acc gac cag acc tgc acg atc gag gac      147
Ile Val Ile Thr Gly Thr Ile Thr Asp Gln Thr Cys Thr Ile Glu Asp
                 30                  35                  40 ccg agc ccc ggt tac atc aag gtc gtg cac ctg ccc acg atc tcc aag      195
Pro Ser Pro Gly Tyr Ile Lys Val Val His Leu Pro Thr Ile Ser Lys
             45                  50                  55 agc gcg ctg aag aac gcc ggc gac gtg gcg ggg cgc act cgc ttc gat      243
Ser Ala Leu Lys Asn Ala Gly Asp Val Ala Gly Arg Thr Arg Phe Asp
         60                  65                  70 atc aag ctg aag gac tgc ccg acc acc gtc aac act ctc aag ctg tac      291
Ile Lys Leu Lys Asp Cys Pro Thr Thr Val Asn Thr Leu Lys Leu Tyr
     75                  80                  85 ttc gag ccc ggc ccc acc acg gat tac ggc acc aag gat ctg aaa gcc      339
Phe Glu Pro Gly Pro Thr Thr Asp Tyr Gly Thr Lys Asp Leu Lys Ala
 90                  95                 100                 105 tat aag cag gct tgg tac gtc gac gcc gca acg ctg ctc aaa tcg ccg      387
Tyr Lys Gln Ala Trp Tyr Val Asp Ala Ala Thr Leu Leu Lys Ser Pro
                110                 115                 120 ccc agt gtg acc gaa gcc aag ggg gtg cag atc cgg ctg atg aac ctg      435
Pro Ser Val Thr Glu Ala Lys Gly Val Gln Ile Arg Leu Met Asn Leu
            125                 130                 135 aac ggc aag cag att ccc atg ggc gag acc gag ccc aac cag cat gcc      483
Asn Gly Lys Gln Ile Pro Met Gly Glu Thr Glu Pro Asn Gln His Ala
```

-continued

```
                 140                 145                 150
gcg gca ttt tcc ggc acc atg caa gcc ggc cag gga cag aaa tcg ttc    531
Ala Ala Phe Ser Gly Thr Met Gln Ala Gly Gln Gly Gln Lys Ser Phe
    155                 160                 165 acc ttg cac tac ctg gcc ggc tac gtg aag aag gcc agt gga gag gtc    579
Thr Leu His Tyr Leu Ala Gly Tyr Val Lys Lys Ala Ser Gly Glu Val
170                 175                 180                 185 gag gcg acc atg ctg acc acc tac gtg ggc ttt tcg gtc gtc tac ccc    627
Glu Ala Thr Met Leu Thr Thr Tyr Val Gly Phe Ser Val Val Tyr Pro
                190                 195                 200 tgaaacgcaa ccatggcggc cgcgttgcgc cctgcgaacc ccggcgatca gcgcggccgc    687
ttgtcgatga gccgccgcgc cttgcccgtc agggtacgct cgacgaagcc cgtgtcggca    747
acctgcacgc gggcgctgac gccgatgtat gacttgaccg catgctgcag ctgcttgccc    807
aggccggcgc gctcggcctc ggtcagggtg agaattc    845
```

<210> SEQ ID NO 11
<211> LENGTH: 201
<212> TYPE: PRT
<213> ORGANISM: Bordetella bronchiseptica - Fim x

<400> SEQUENCE: 11

```
Met Gln Ala Lys Thr Phe Leu Leu Gly Ala Ala Leu Ala Gly Val Ala
1               5                   10                  15

Leu Ala Ala His Ala Glu Asp Gly Thr Ile Val Ile Thr Gly Thr Ile
                20                  25                  30

Thr Asp Gln Thr Cys Thr Ile Glu Asp Pro Ser Pro Gly Tyr Ile Lys
            35                  40                  45

Val Val His Leu Pro Thr Ile Ser Lys Ser Ala Leu Lys Asn Ala Gly
        50                  55                  60

Asp Val Ala Gly Arg Thr Arg Phe Asp Ile Lys Leu Lys Asp Cys Pro
65                  70                  75                  80

Thr Thr Val Asn Thr Leu Lys Leu Tyr Phe Glu Pro Gly Pro Thr Thr
                85                  90                  95

Asp Tyr Gly Thr Lys Asp Leu Lys Ala Tyr Lys Gln Ala Trp Tyr Val
            100                 105                 110

Asp Ala Ala Thr Leu Leu Lys Ser Pro Pro Ser Val Thr Glu Ala Lys
        115                 120                 125

Gly Val Gln Ile Arg Leu Met Asn Leu Asn Gly Lys Gln Ile Pro Met
    130                 135                 140

Gly Glu Thr Glu Pro Asn Gln His Ala Ala Phe Ser Gly Thr Met
145                 150                 155                 160

Gln Ala Gly Gln Gly Gln Lys Ser Phe Thr Leu His Tyr Leu Ala Gly
                165                 170                 175

Tyr Val Lys Ala Ser Gly Val Glu Ala Thr Met Leu Thr Thr
            180                 185                 190

Tyr Val Gly Phe Ser Val Val Tyr Pro
        195                 200
```

<210> SEQ ID NO 12
<211> LENGTH: 960
<212> TYPE: DNA
<213> ORGANISM: Bordetella bronchiseptica - Fim a
<220> FEATURE:
<221> NAME/KEY: CDS
<222> LOCATION: (286)..(888)
<223> OTHER INFORMATION:

<400> SEQUENCE: 12

```
atgcgccggt caatgccggc caacggcgcc gcctttccgc cctattgaag cccatccttt    60
tggatgggct ttttgttgaa atttcctaca cgatcaattg aattggacta cgcgtaattg   120
cgcgtaggac tgcaggaaag ttggatgaga atttttagaa ttcttcccgt tgttgatttg   180
tttccttcat ctctagatga atattcccag gcatcggact ccattcctgg attcgttttt   240
cacggagcgc cgatcgcctg gttttcggat aacagggggt cgatc atg aat ctc aaa   297
                                              Met Asn Leu Lys
                                                1
```

| | | | | | | | | | | | | | | | | |
|---|---|---|---|---|---|---|---|---|---|---|---|---|---|---|---|---|
| ttt | gca | gga | atc | gca | ctg | ggc | ctg | acc | gcc | tgt | gca | ttg | acg | tac | cag | 345 |
| Phe | Ala | Gly | Ile | Ala | Leu | Gly | Leu | Thr | Ala | Cys | Ala | Leu | Thr | Tyr | Gln | |
| 5 | | | | 10 | | | | | 15 | | | | | 20 | | |

| cat | cag | gtt | ttc | gcg | gcg | gac | ggc | acg | ctc | gtg | att | acc | ggc | gcc | atc | 393 |
|---|---|---|---|---|---|---|---|---|---|---|---|---|---|---|---|---|
| His | Gln | Val | Phe | Ala | Ala | Asp | Gly | Thr | Leu | Val | Ile | Thr | Gly | Ala | Ile | |
| | | | 25 | | | | 30 | | | | | 35 | | | | |

| acg | gat | acg | acg | tgc | aag | atc | aat | ggc | gcg | gag | cct | ccc | acc | aac | ata | 441 |
|---|---|---|---|---|---|---|---|---|---|---|---|---|---|---|---|---|
| Thr | Asp | Thr | Thr | Cys | Lys | Ile | Asn | Gly | Ala | Glu | Pro | Pro | Thr | Asn | Ile | |
| | 40 | | | | | 45 | | | | | 50 | | | | | |

| gcg | gtg | caa | ttg | ccg | acc | att | tcg | cgc | acc | gcg | ctc | aag | gac | gta | ggg | 489 |
|---|---|---|---|---|---|---|---|---|---|---|---|---|---|---|---|---|
| Ala | Val | Gln | Leu | Pro | Thr | Ile | Ser | Arg | Thr | Ala | Leu | Lys | Asp | Val | Gly | |
| 55 | | | | | 60 | | | | | 65 | | | | | | |

| tcg | acg | gca | ggc | ggg | aca | gtt | ttt | gac | gtg | aaa | ctg | acc | gag | tgt | ccg | 537 |
|---|---|---|---|---|---|---|---|---|---|---|---|---|---|---|---|---|
| Ser | Thr | Ala | Gly | Gly | Thr | Val | Phe | Asp | Val | Lys | Leu | Thr | Glu | Cys | Pro | |
| 70 | | | | | 75 | | | | | 80 | | | | | | |

| cag | gca | ttg | aat | ggt | cag | caa | gtg | gga | ttg | ttc | ttc | gaa | cct | ggt | ggc | 585 |
|---|---|---|---|---|---|---|---|---|---|---|---|---|---|---|---|---|
| Gln | Ala | Leu | Asn | Gly | Gln | Gln | Val | Gly | Leu | Phe | Phe | Glu | Pro | Gly | Gly | |
| 85 | | | | 90 | | | | | 95 | | | | | 100 | | |

| acg | gtt | gac | tat | acg | tcg | gga | aat | ctg | ttt | gcg | tac | cgg | gcc | gat | agt | 633 |
|---|---|---|---|---|---|---|---|---|---|---|---|---|---|---|---|---|
| Thr | Val | Asp | Tyr | Thr | Ser | Gly | Asn | Leu | Phe | Ala | Tyr | Arg | Ala | Asp | Ser | |
| | | | | 105 | | | | | 110 | | | | | 115 | | |

| cag | ggc | gta | gaa | cag | gtg | ccg | cag | acg | aaa | gcc | gac | aac | gtg | caa | ttc | 681 |
|---|---|---|---|---|---|---|---|---|---|---|---|---|---|---|---|---|
| Gln | Gly | Val | Glu | Gln | Val | Pro | Gln | Thr | Lys | Ala | Asp | Asn | Val | Gln | Phe | |
| | | 120 | | | | | 125 | | | | | 130 | | | | |

| cag | ctt | gcc | aat | ctg | gat | ggt | tcc | gcc | att | cat | ttg | ggt | cgc | aac | aag | 729 |
|---|---|---|---|---|---|---|---|---|---|---|---|---|---|---|---|---|
| Gln | Leu | Ala | Asn | Leu | Asp | Gly | Ser | Ala | Ile | His | Leu | Gly | Arg | Asn | Lys | |
| | 135 | | | | | 140 | | | | | 145 | | | | | |

| ggt | gcg | cag | gct | gct | cag | acg | ttt | ctg | gta | tcg | cag | acg | gca | ggg | tcg | 777 |
|---|---|---|---|---|---|---|---|---|---|---|---|---|---|---|---|---|
| Gly | Ala | Gln | Ala | Ala | Gln | Thr | Phe | Leu | Val | Ser | Gln | Thr | Ala | Gly | Ser | |
| 150 | | | | | 155 | | | | | 160 | | | | | | |

| tcg | acg | tac | ggg | acg | acc | ctg | cgc | tat | ctg | gca | cgc | tac | atc | cgt | tcg | 825 |
|---|---|---|---|---|---|---|---|---|---|---|---|---|---|---|---|---|
| Ser | Thr | Tyr | Gly | Thr | Thr | Leu | Arg | Tyr | Leu | Ala | Arg | Tyr | Ile | Arg | Ser | |
| 165 | | | | 170 | | | | | 175 | | | | | 180 | | |

| ggc | gct | ggc | tcc | atc | gtt | gcg | ggg | aat | ctc | cgc | agc | cag | gtg | ggg | ttc | 873 |
|---|---|---|---|---|---|---|---|---|---|---|---|---|---|---|---|---|
| Gly | Ala | Gly | Ser | Ile | Val | Ala | Gly | Asn | Leu | Arg | Ser | Gln | Val | Gly | Phe | |
| | | | 185 | | | | | 190 | | | | | 195 | | | |

| tcc | gtg | atg | tat | ccg | tagcccgtga | aagaggggcc | gcccattgcg | gggggccccg | 928 |
|---|---|---|---|---|---|---|---|---|---|
| Ser | Val | Met | Tyr | Pro | | | | | |
| | | 200 | | | | | | | |

```
gtacgggatg tcggcttgt cacgagattc tt                                   960

<210> SEQ ID NO 13
<211> LENGTH: 201
<212> TYPE: PRT
<213> ORGANISM: Bordetella bronchiseptica - Fim a

<400> SEQUENCE: 13

Met Asn Leu Lys Phe Ala Gly Ile Ala Leu Gly Leu Thr Ala Cys Ala
1               5                   10                  15
```

```
Leu Thr Tyr Gln His Gln Val Phe Ala Ala Asp Gly Thr Leu Val Ile
         20                  25                  30

Thr Gly Ala Ile Thr Asp Thr Thr Cys Lys Ile Asn Gly Ala Glu Pro
             35                  40                  45

Pro Thr Asn Ile Ala Val Gln Leu Pro Thr Ile Ser Arg Thr Ala Leu
 50                  55                  60

Lys Asp Val Gly Ser Thr Ala Gly Gly Thr Val Phe Asp Val Lys Leu
 65                  70                  75                  80

Thr Glu Cys Pro Gln Ala Leu Asn Gly Gln Gln Val Gly Leu Phe Phe
                 85                  90                  95

Glu Pro Gly Gly Thr Val Asp Tyr Thr Ser Gly Asn Leu Phe Ala Tyr
             100                 105                 110

Arg Ala Asp Ser Gln Gly Val Glu Val Pro Gln Thr Lys Ala Asp
             115                 120                 125

Asn Val Gln Phe Gln Leu Ala Asn Leu Asp Gly Ser Ala Ile His Leu
130                 135                 140

Gly Arg Asn Lys Gly Ala Gln Ala Ala Gln Thr Phe Leu Val Ser Gln
145                 150                 155                 160

Thr Ala Gly Ser Ser Thr Tyr Gly Thr Thr Leu Arg Tyr Leu Ala Arg
                 165                 170                 175

Tyr Ile Arg Ser Gly Ala Gly Ser Ile Val Ala Gly Asn Leu Arg Ser
             180                 185                 190

Gln Val Gly Phe Ser Val Met Tyr Pro
             195                 200

<210> SEQ ID NO 14
<211> LENGTH: 50
<212> TYPE: DNA
<213> ORGANISM: Bordetella bronchiseptica

<400> SEQUENCE: 14
gggttcctac atatctatca gcccccccc ccggcgaact ctaatattct            50

<210> SEQ ID NO 15
<211> LENGTH: 55
<212> TYPE: DNA
<213> ORGANISM: Bordetella bronchiseptica

<400> SEQUENCE: 15
gggttcctac atatctatca gcccccccc ccccggcgaa ctctaatatt attct      55

<210> SEQ ID NO 16
<211> LENGTH: 51
<212> TYPE: DNA
<213> ORGANISM: Bordetella pertussis

<400> SEQUENCE: 16
tgtttcccac atcggaatca gcccccccc ccccccccta agacctaaga t          51

<210> SEQ ID NO 17
<211> LENGTH: 40
<212> TYPE: DNA
<213> ORGANISM: Bordetella pertussis

<400> SEQUENCE: 17
aaattcctac acatccatca gcccccccga ggcgtctaat                      40

<210> SEQ ID NO 18
<211> LENGTH: 45
```

-continued

```
<212> TYPE: DNA
<213> ORGANISM: Bordetella pertussis

<400> SEQUENCE: 18
aaattcccac acaaccatca gcccccgccc cggacctgat attct                45

<210> SEQ ID NO 19
<211> LENGTH: 52
<212> TYPE: DNA
<213> ORGANISM: Bordetella bronchiseptica

<400> SEQUENCE: 19
tgtttcccac atcggaatca gcccccgccc ccccccccct aagacctaag at        52

<210> SEQ ID NO 20
<211> LENGTH: 54
<212> TYPE: DNA
<213> ORGANISM: Bordetella bronchiseptica

<400> SEQUENCE: 20
aaattcccac acaaccatca gcccccgccc ccccccccc ggacctaata ttct       54

<210> SEQ ID NO 21
<211> LENGTH: 53
<212> TYPE: DNA
<213> ORGANISM: Bordetella bronchiseptica

<400> SEQUENCE: 21
aattcctaga tacccatgag gcccccgccc ccccctgagg cgtccaataa tct       53
```

POLYNUCLEOTIDES ENCODING *BORDATELLA BRONCHISEPTICA* FIMBRIAL PROTEINS (FIMN), VECTORS, AND EXPRESSION SYSTEMS THEREFOR

CROSS-REFERENCE TO A RELATED APPLICATION

This application claims the benefit of U.S. Provisional Application No. 60/134,181 filed May 14, 1999

The subject invention was made with government support under Grant No. TENV1433BEMIS99 awarded by the United States Department of Agriculture. The government has certain rights in this invention.

BACKGROUND OF THE INVENTION

*Bordetella bronchiseptica* is an etiologic agent of infectious tracheobronchitis (Kennel Cough) in dogs, atrophic rhinitis in pigs, and respiratory infections in rabbits and guinea pigs. Bordetella infections depress the respiratory clearance mechanisms (mucociliary elevator), facilitating invasion by other organisms. Colonization of the upper respiratory tract by the bacteria occurs via firm attachment to the ciliated respiratory epithelium, followed by rapid proliferation and an inflammatory response. Binding to host tissue is the primary step in the establishment of infection, and *B. bronchispetica* produce an array of moleculesthat mediate attachment, including filamentous hemagglutinin, tracheal cytotoxin, pertactin, and fimbriae. Several genes coding for fimbrial subunits have been previously reported, including fim 2, fim 3, fim A, and fim X. Most of these fimbrae have counterparts in *B. pertussis*.

Two fimbrial phenotypes of *B. bronchiseptica* have been defined serologically as fim 2 and fim 3. They are reactive with factor specific antiserums historically used for serotyping *B.pertussis* isolates. Fim A and fim X (Boschwitz, J. S., H. G. J. van der Heide, F. R. Mooi, and D. A. Relman [1997] *J. Bacteriol.* 179:7882–7885), two other major fimbrial proteins, are also expressed in *B.bronchiseptica*; however, their antigenic characteristics are not known. Existence of other bordetella fimbriae has been hypothesized (Mooi, F. R., W. H. Jansen, H. Brunings, H. Gielen, H. G. J van der Heide, H. C. Walvoort, and Guinee, P. A. M. [1992] *Micro. Pathog.* 12:127–135).

The expression of bordetella fimbrial genes is positively regulated through the bvg locus (Willems, R., A. Paul, H. G. J. van der Heide, A. R. ter Avest, and F. R. Mooi [1990] *EMBO J.* 9:2803–2809) and their promoter regions have in common a stretch of cytosines referred to as a C-stretch (Willems et al. [1990] supra; Riboli, B., P. Pedroni, A. Cuzzoni, and F. de Ferra [1991] *Micro. Pathog.* 10:393–403), and two motifs 5' to the C-stretch comprising an ABR or fim box (Riboli et al., [1991] supra). Characterization of fimbrial genes and their products is important to the understanding of fimbrial gene regulation, for serological diagnosis, for identification of potential subunit vaccine candidates, and to understand mechanisms of cellular adhesion.

BRIEF SUMMARY OF THE INVENTION

The subject invention concerns novel polynucleotides of Bordetella species, and the polypeptides encoded thereby. The subject invention further provides vaccines useful for providing protection against Bordetella infections.

In a specific embodiment, the subject invention provides a unique *Bordetella bronchiseptica* gene. This gene was isolated from a cosmid constructed with *B. bronchiseptica* chromosomal DNA. This cosmid, when introduced into attachment deficient *B. bronchiseptica*, increases the binding of the bacteria to epithelial cells. The fimbrial gene, referred to as fim N, has been subcloned and sequenced. The predicted protein from this gene has about 59% and about 52% homology with *B. bronchiseptica* fim 2 and fim 3, respectively. Fim N encodes a protein predicted to be similar in size and structure to those encoded by fim 2 and fim 3. Serologically, the fim N protein appears to have cross-reactivity with serotype 2 antibodies. The fim N protein is present in *B. bronchiseptica* isolates associated with disease in several species of veterinary importance.

Various abbreviations are found within this specification. Their terms and meanings are as follows: aa, amino acid(s); Ab, antibody(ies); Ap, ampicillin; ELISA, enzyme-linked immunosorbent assay; EtdBr, ethidium bromide; IPTG, isopropyl β-D-thiogalactopyranoside; kb, kilobase; LB, Luria-Bertani (medium); mAB, monoclonal Ab; Ni—-NTA, nickel-nitrilotriacetic acid; nt, nucleotide(s); O.D., optical density; oligo, oligonucleotide; ORF, open reading frame; p, plasmid; PCR, polymerase chain reaction; PBS, phosphate buffered saline; PBSTW, PBS containing polyoxyethylene-sorbitan monolaurate; SDS-PAGE, sodium dodecyl sulfate polyacrylamide gel electrophoresis; Tc, tetracycline.

BRIEF DESCRIPTION OF THE DRAWINGS

FIG. 1 shows a comparison of the DNA sequences of *Bordetella bronchiseptica* fimbrial genes fim 2 SEQ ID NO:8, fim 3 SEQ ID NO:6 and fim N SEQ ID NO:3.

FIG. 2 shows a comparison of *Bordetella bronchiseptica* fimbrial proteins fim 2 SEQ ID NO:9, fim 3 SEQ ID NO:7, fim X SEQ ID NO:11, fim A SEQ ID NO:13 and fim N SEQ ID NO:4 predicted from DNA sequences.

FIG. 4 shows the fim N DNA sequence and predicted protein from *B. bronchiseptica*. The DNA sequence is identical in plasmids pBS84 and pGB710, as well as chromosomal *B. bronchiseptica* 110H (the source of the plasmids) and from *B. bronchiseptica* strain 64-C-0406. The putative signal sequence is shown in bold and the probe originally used to identify the gene in transfected *E.coli*. is underlined.

FIG. 5 shows a comparison of *B.bronchiseptica* fim N with other fimbrial proteins. Comparisons of homology were made using the gap program in the GCG software package. The sequences used for these comparisons were obtained from the following GenBank entries: *B.pertussis* fim 2, FM2_BORPE; *B.bronchiseptica* fim 2, BBFIM2; *B.pertussis* fim X, BPFIMX; *B.bronchiseptica* fim 3, BBFIM3, *B.pertussis* fim 3, S12578; and *B.bronchiseptica* fim X, S36451.

FIG. 6 shows the putative fim N promoter region compared to other fim promoters. Alignment of the 5' and 3' activator binding regions and "C-stretch" characteristic of Bordetella fimbrial promoters regulated by by genes. The activator binding regions are marked by boxes A (5') and B (3'). The C-stretches are underlined, and the −10 regions are shown with a double underline.

FIG. 7 shows the attachment of *Bordetella bronchiseptica* to Vero cells. Results shown represent the binding of bacteria to Vero cells and are the means of triplicate samples plus or minus the standard deviations. The lesion in the spontaneously occuring mutant, strain 110NH, is localized in the Bvg locus as determined by complementation studies with a cloned Bvg gene (Burns, E. H., Jr. [1995] "Involvement of serotype 2 fimbriae in attachment by *Bordetella bronchiseptica*" dissertation, Univ. Tennessee).

DETAILED DESCRIPTION OF THE INVENTION

Figure 3:
FIG. 3 shows SDS-PAGE analysis of fim N recombinant protein. Proteins were separated by electrophoresisin 10% SDS-PAGE. Lane 1; MBP-fim N recombinant protein, lane 2; MBP standard, lane 3; MBP-fim N recombinant protein treated with factor Xa to separate the fusion proteins.

The subject invention pertains to Bordetella species fimbrial proteins and genes, and their use as vaccines. One aspect of the subject invention pertains to the fimbrial protein (fim N) found in the bacterium, *Bordetella bronchiseptica*.

The proteins and polynucleotides of the subject invention can be used to produce an immune response, such as antibody or cytokine production, by administration of the protein or polynucleotides to an animal. In one embodiment, the subject invention concerns the use of fim N as an immunogenic vaccine component to protect against Bordetella infections. In a further embodiment the fim N protein is used as a fusion partner with heterologous antigens in vaccine compositions.

Serotype 2 cross-reactive fimbrial are abundant, immunodominant surface fibrils present on many wild-type strains of *B. bronchiseptica* and are involved in bacterial attachment to host surfaces. There is a redundancy of attachment proteins present in most *B. bronchiseptica* strains; however, specific anti-fimbrial antibodies reactive with serotype 2 fimbrial have been found to reduce bacterial attachment. Fim N possesses a major epitope shared with fim 2 of *Bordetella pertussis* and recognized by monoclonal antibodies BpF2, BPA10, and BPA5, making the subject protein a useful component for acellular human pertussis vaccines.

The fimbrial gene disclosed herein, fim N, contains all of the features associated with bvg regulated expression and is distinct from previously reported fimbrial genes of Bordetella species.

The subject invention provides a previously unidentified *B.bronchiseptica* gene, fimN, encoding a fimbrial protein. The sequence of fimN is distinct from, previously reported fimbrial subunit genes of *B. bronchiseptica* including fimA, fim2, fim3, and fimX.

The putative promoter region of fimN contains a stretch of cytosines, termed a C-stretch (Riboli et al. [1991] supra), that is characteristic of the promoter region of *B. bronchiseptica* and *B. pertussis* fimbrial genes. It is interesting to note that *B. bronchiseptica* chromosomal DNA contains two more cytosine residues in its C-stretch than the cloned gene. The length of the C-stretch is important because genes with longer C-stretches have been shown to have enhanced gene expression (Willems et al. [1990] supra; Riboli et al. [1991] supra). Changes in the length of the C-stretch may be used as a mechanism for regulation of fim gene expression (Willems et al. [1990] supra). The promoter region of fimN also contains the two regions comprising the ABR motif. The 5' section of the ABR is identical to that of *B.pertussis* fimX and differs from fim2 and fim3 by one nucleotide. The 3' portion of the ABR is identical among fimN, fimX, fim2, and fim3 with the exception of *B.bronchiseptica*fimX. The lack of homology of fimX with the 3' portion of the ABR of the other genes is not surprising because it has never been shown to be expressed. Bvg regulation of fimN seems likely because the ABR, C-stretch, and 20 bp upstream from the initiation codon are sufficient, in the case of the bvg regulated fim3 promoter, for protein expression (Riboli et al. [1991] supra). The fimN gene was contained within a cosmid constructed from *B. bronchiseptica* chromosomal DNA.

Historically, the classification of Bordetella fimbrial proteins has been based on serological reactivity. mAB reactive with serotype 2 and both serotype 2 and 3 fimbrae react with fimN. One of the mAB, BpA10, shows some cross-reactivity with type 3 subunits on western blots. A further classification scheme involves relatedness at the genetic or peptide level. Among *B.bronchiseptica* fimbrial proteins, fimN is most closely related to fim2 and fim3, and is essentially as similar in amino acid sequence to these proteins as they are to each other (53.4%). It is interesting to note that fimN has slightly greater homology to fim2 and fim3 of *B. pertussis* than to the analogous *B. bronchiseptica* proteins. This association is even more pronounced when the comparison is done with the putative mature protein, lacking the signal peptide. Conservation of the fimN sequence, deduced from two different *B.bronchiseptica* isolates, suggests that this protein is not restricted to a single isolate and that its function is important for the survival of the organism.

Recombinant fim N protein produced in *E. coli* can be concentrated as insoluble inclusion bodies, crude preparations of which can be adapted to veterinary vaccine applications. A methodology of protein solubilization has been devised which, when coupled with a commercially available affinity purification system, produces a homogenous 26 kd fusion protein in relatively high yield. One recombinant construct comprises a 593 bp coding region of fim N, without signal sequence, flanked by histidine residues. The purified recombinant fim N protein reacts with fim 2-specific antibodies and can elicit antibodies that react with native protein. Recombinant fim N can be used as an injectable acellular vaccine component for animals. Functional adhesive properties of purified recombinant fim N protein make it useful as an acellular vaccine product that can be directly instilled into the respiratory tract.

In a further aspect of the subject invention, fim N can be used as a carrier molecule for other antigens, to stabilize other antigens, or to stabilize protein compositions. Compositions comprising proteins or antigens (secondary antigens) may be stabilized by the addition of fim N to compositions comprising antigen(s) or protein(s) which one desires to stabilize. Alternatively, antigen or protein stabilization may be accomplished by fim N conjugation to a secondary antigen, molecule, or protein. Fim N conjugation can have the benefit of stabilizing the secondary antigen and protecting it from degradation. Fim N may be conjugated to a secondary antigen using well-known chemical cross-linking agents (see, for example, the Pierce Catalog and Handbook, The Pierce Chemical Company [1994]) or by recombinant fusion to a secondary antigen. Furthermore, fim N can act as an adjuvant enhancing the immune response of a secondary antigen. Fim N can also facilitate delivery of a secondary antigen to the respiratory tract. For example, in one embodiment, a 663 bp carboxy terminal fragment of *Pasteurella hemolytica* leukotoxin (LTX) was fused to the 534 bp coding region of fim N. The 72 kd fusion protein retained the antigenicity of its original components. LTX, noted for its lability in storage, even when in fusion with another protein (such as GST), was stable in storage for extended periods, and when injected into mice and rabbits, produced high levels of antibodies that neutralized the activity of native leukotoxin and reacted with native fimbriae. Mice immunized with GST-LTX-FIM stored for up to six (6) months produced immune responses equivalent to those produced in mice immunized with freshly prepared GST-LTX-FIM.

In yet another embodiment of the subject invention, recombinant fim N can be expressed in avirulent Bordetella strains for use as live attenuated intranasal vaccines. Recombinant fim N polynucleotide, with its own promoter region, has been constructed on a broad host range, cryptic plasmid that was originally isolated from Bordetella. This plasmid is very stable in Bordetella, even in the absence of selection. Using the methods and materials of the present invention, many different antigens can be delivered to the respiratory tract in this fashion. Live attenuated *B. bronchiseptica* intranasal vaccines have been in widespread use for dogs and pigs. Commercial *B. bronchiseptica* whole-cell bacterins and acellular extract vaccines are used in dogs, cats and pigs. In addition to providing new vaccines for these animals, *B. bronchiseptica* infects many other mammalian species and, therefore, can be used as an antigen delivery system in numerous other animals and systems.

Yet another embodiment of the subject invention pertains to a recombinant GST:LTX:FIM N fusion protein for use in ruminants as a protective immunogen against shipping fever pneumonia and other infections caused by *Pasteurella hemolytica*. Compared to GST:LTX alone, the fusion protein containing fim N, provides greater yields, gives greater stability to LTX and results in higher levels of leukotoxin neutralizing antibodies in immunized animals. LTX neutralizing antibody levels in the serum of immunized animals were significantly higher in groups of mice immunized with GST-LTX-FIM than in animals immunized with GST-LTX-GST or GST-LTX ($p<0.03$ to $0.001$). Interestingly, these results were independent of the type or presence of additional adjuvants, such as complete or incomplete Freund's adjuvant. The correlation between neutralizing antibodies and protection against *P. hemolytica* induced pneumonia in cattle is well documented; therefore, the recombinant GST:LTX:FIM N protein provides an improved purified protective antigen.

Cosmid clones bearing the initial fim N inserts restored fim 2 antigen reactivity and attachment levels in naturally deficient strains of *B. bronchiseptica* to levels comparable to the strain from which fim N was originally isolated. Hybridization studies with oligonucleotide probes have indicated that other fimbrial genes and adhesins (FHA and pertactin) are not present in the inserts. The 534 bp coding region of fim N, without signal sequence, has been expressed in *E. coli* as a fusion protein with the histidine residues from the IPTG inducible trc promoter following inframe cloning of an amplified PCR product in pPROEX TM HT vector(Gibco). The resultant 26 kd fusion protein was purified under denaturing conditions using NI-NTA resin and refolded by dialysis. The purified protein produced a single band in PAGE and reacted with monoclonal antibodies specific for *B. pertussis* denatured fim 2 monomers but did not react with CF8 antibody which recognizes native protein.

In preparation to express fim N in *B. bronchiseptica*, the fim N coding region and a 170 bp upstream region predicted to contain the fim promoter were subcloned into the broad host range vector, pBBR 1.

To evaluate the ability to use fim N as a heterologous antigen carrier, a 663 bp polynucleotide encoding a carboxy terminal fragment of *Pasteurella hemolytica* leukotoxin (ltx) was amplified by PCR and cloned in pGEX-5X (Pharmacia Biotech). The LTX peptide was expressed in fusion with Glutathione-S-transferase(GST) under control of inducible tac promoter. A 72 kd recombinant protein was expressed in *E. coli* after cloning fim N (without signal sequence) downstream of the ltx construct. The protein was purified to produce a single band on PAGE and it reacted with both leukotoxin- and fimbrial-specific antibodies by ELISA and western blot. The GST-LTX-FIM fusion provided greater yields and in vitro stability of the LTX antigen and resulted in higher levels of LTX neutralizing antibodies in mice than that which is obtained from immunization with GST-LTX.

In accordance with the subject invention, fim N:heterologous antigen fusion proteins can be readily prepared and these recombinants retain the antigenic and immunogenic properties of their individual components. Furthermore, the hydrophobic nature of the fim N protein makes it a more generally desirable adjuvant.

The subject invention also pertains to vectors comprising polynucleotide sequences of the present invention. These vectors include, for example, cloning vectors, expression vectors and the like. Numerous vectors which can be used according to the present invention are known in the art.

Also contemplated by the present invention are cells, microorganisms, viruses and the like that comprise the polynucleotides and/or polypeptides of the invention. The cells can be either eukaryotic or prokaryotic cells. Prokaryotic cells include, for example, *E coli*, Bacillus species and others. Eukaryotic cells include, for example, yeast cells, insect cells, plant cells, and mammalian cells. Microorganisms and cells comprising polynucleotides of the invention can be used to express sufficient quantities of the fimbrial protein for purification purposes.

The subject invention also concerns antibodies that bind to polypeptides of the invention. Antibodies that are immunospecific for fim N protein of the invention are specifically contemplated. Antibodies which do not cross react with other fimbrial proteins are also specifically contemplated. The antibodies of the subject invention can be prepared using standard materials and methods known in the art (see, for example, *Monoclonal Antibodies: Principles and Practice*, 1983; *Monoclonal Hybridoma Antibodies: Techniques and Applications*, 1982; *Selected Methods in Cellular Immunology*, 1980; *Immunological Methods, Vol. II*, 1981; *Practical Immunology*, and Kohler et al. [1975] *Nature* 256:495). The antibodies of the subject invention are useful in assays for the identification of organisms expressing fimbrial proteins (serotyping), diagnosis of animals infected by organisms expressing fimbrial proteins, and treating animals infected by organisms which express fimbrial proteins.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity, particularly neutralizing activity. "Antibody fragments" comprise a portion of a fall length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. [1975] *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. [1991] *Nature* 352: 624–628 and Marks et al. [1991] *J. Mol. Biol.* 222: 581–597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. [1984] *Proc. Natl. Acad Sci. USA* 81: 6851–6855).

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies [1994] Vol. 113:269–315, Rosenburg and Moore eds. Springer-Verlag, New York.

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). Diabodies are described more fully in, for example, EP 404,097; WO 93/11161; and Hollinger et al. [1993] *Proc. Natl. Acad. Sci. USA* 90: 6444–6448.

The term "linear antibodies" refers to the antibodies described in Zapata et al. [1995] *Protein Eng.* 8(10):1057–1062.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Treatment" refers to both therapeutic treatment and prophylactic or preventative measures. Those in need of treatment include those already infected by organisms to which antibodies of this invention specifically immunoreact as well as those in which the infection is to be prevented. "Treatment" includes the use of antibodies linked to cytotoxic or chemotherapeutic agents by chemical or genetic means.

Antibodies of this invention may be chemically or genetically linked to cytotoxic or chemotherapeutic agents according to methods well known in the art (see for example the Pierce Catalog and Handbook) for the construction of immuntherapeutic agents. Numerous patents teach genetically constructed immunotoxins. These immunotherapeutic agents are useful for the treatment of animals infected by organisms expressing fimbrial proteins with which the antibodies of the invention specifically immunoreact.

Antibodies of the invention may also be chemically linked to labels and used in serotyping or diagnostic assays known in the art for the detection of organisms expressing fimbrial proteins with which antibodies of this invention specifically immunoreact.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of Gram negative bacterial infections, such as antibiotics, toxins, and combinations thereof. Examples of chemotherapeutic agents include antibiotic classes useful against Gram negative organisms. These include, and are not limited to, penicillins, aminoglycosides, cephalosporins, tetracyclines, vancomycins, chloramphenicol, erythromycins, clindamycin, lincomycin, polymixins, bacitracin, trimethoprim, sulfamethoxazole, and sulfonamids and derivatives thereof.

The term "prodrug" as used in this application refers to a precursor or derivative form of a pharmaceutically active substance that is less cytotoxic to bacterial cells compared to the parent drug and is capable of being enzymatically activated or converted into the more active parent form.

The word "label" when used herein refers to a detectable compound or composition which is conjugated directly or indirectly to the antibody. The label may itself be detectable by itself (e.g., radioisotope labels, labels detectable by NMR, or fluorescent labels) or, in the case of an enzymatic label, may catalyze chemical alteration of a substrate compound or composition which is detectable. The "label" may be linked to the antibody through a ligand and its receptor, for example avidin and biotin, such as those described in U.S. Pat. No. 5,608,060 hereby incorporated by reference in its entirety.

The subject invention also concerns oligonucleotide primers and probes that can hybridize to a polynucleotide of the subject invention. The oligonucleotide primers and probes can be used to detect or identify fim N sequences or sequences related to fim N.

As those of ordinary skill in the art will appreciate, any of a number of different nucleotide sequences can be used, based on the degeneracy of the genetic code, to produce the fimbrial proteins described herein. Accordingly, any nucleotide sequence which encodes the fimbrial proteins described herein comes within the scope of this invention and the claims appended hereto. Also, as described herein, fragments of the fimbrial proteins are an aspect of the subject invention so long as such fragments retain substantially the same biological activity as full length protein. Such fragments can easily and routinely be produced by techniques well known in the art. For example, time-controlled Bal31 exonuclease digestion of the full-length DNA followed by expression of the resulting fragments and routine screening methods can be used to readily identify expression products having the desired activity (Wei et al., 1983).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. Allelic variations of the exemplified sequences also come within the scope of the subject invention. The polynucleotide sequences falling within the scope of the subject invention further include sequences which specifically hybridize with the exemplified sequences. The polynucleotide includes both the sense and antisense strands as either individual strands or in the duplex.

The polynucleotide sequences may also be used to isolate full length clones of genes which encode other fimbrial proteins similar to those which are specifically exemplified herein. The subject invention provides unique polynucleotides which have been identified as novel fibrial genes. The invention also comprises polynucleotides which are complementary to the disclosed polynucleotide sequences.

Also contemplated in this invention is the use of oligomers from these sequences in a kit which can be used to identify a gene encoding a fimbrial protein. The invention also provides detection systems for genes encoding fimbrial proteins in other procaryotic organisms.

"Probes" are nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

"Reporter" molecules are chemical moieties used for labelling a nucleic or amino acid sequence. They include, but are not limited to, radionuclides, enzymes, fluorescent, chemi-luminescent, or chromogenic agents. Reporter molecules associate with, establish the presence of, and may allow quantification of a particular nucleic or amino acid sequence.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labelled with reporter molecules using nick translation, Klenow fill-in reaction, PCR or other methods well known in the art. After pretesting to optimize reaction conditions and to eliminate false positives, nucleic acid probes may be used in Southern, northern or in situ hybridizations to determine whether DNA or RNA encoding the protein is present in a biological sample, cell type, tissue, organ or organism.

"Linkers" are synthesized palindromic nucleotide sequences which create internal restriction endonuclease sites for ease of cloning the genetic material of choice into various vectors. "Polylinkers" are engineered to include multiple restriction enzyme sites and provide for the use of both those enzymes which leave 5' and 3' overhangs such as BamHI, EcoRI, PstI, KpnI and Hind III or which provide a blunt end such as EcoRV, SnaBI and StuI.

"Control elements" or "regulatory sequences" are those nontranslated regions of the gene or DNA such as enhancers, promoters, introns and 3' untranslated regions which interact with cellular proteins to carry out replication, transcription, and translation. They may occur as boundary sequences or even split the gene. They function at the molecular level and along with regulatory genes are very important in development, growth, differentiation and aging processes.

"Chimeric" molecules are polynucleotides or polypeptides which are created by combining one or more of nucleotide sequences of this invention (or their parts) with additional nucleic acid sequence(s). Such combined sequences may be introduced into an appropriate vector and expressed to give rise to a chimeric polypeptide which may be expected to be different from the native molecule in one or more of the following characteristics: cellular location, distribution, ligand-binding affinities, interchain affinities, degradation/turnover rate, signaling, etc.

"Active" is that state which is capable of being useful or of carrying out some role. It specifically refers to those forms, fragments, or domains of an amino acid sequence which display the biologic and/or immunogenic activity characteristic of the naturally occurring peptide, polypeptide, or protein.

"Naturally occurring" refers to a polypeptide produced by cells which have not been genetically engineered or which have been genetically engineered to produce the same sequence as that naturally produced. Specifically contemplated are various polypeptides which arise from post-transnational modifications. Such modifications of the polypeptide include but are not limited to acetylation, carboxylation, glycosylation, phosphorylation, lipidation and acylation.

"Derivative" refers to those polypeptides which have been chemically modified by such techniques as ubiquitination, labelling (see above), pegylation (derivatization with polyethylene glycol), and chemical insertion or substitution of amino acids such as ornithine which do not normally occur in proteins.

"Recombinant polypeptide variant" refers to any polypeptide which differs from naturally occurring peptide, polypeptide, or protein by amino acid insertions, deletions and/or substitutions, created using recombinant DNA techniques. Guidance in determining which amino acid residues may be replaced, added or deleted without abolishing characteristics of interest may be found by comparing the sequence of the peptide, polypeptide, or protein with that of related polypeptides and minimizing the number of amino acid sequence changes made in highly conserved regions.

Amino acid "substitutions" are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid "insertions" or "deletions" are changes to or within an amino acid sequence. They typically fall in the range of about 1 to 5 amino acids. The variation allowed in a particular amino acid sequence may be experimentally determined by producing the peptide synthetically or by systematically making insertions, deletions, or substitutions of nucleotides in the sequence using recombinant DNA techniques.

A "signal or leader sequence" is a short amino acid sequence which or can be used, when desired, to direct the polypeptide through a membrane of a cell. Such a sequence may be naturally present on the polypeptides of the present invention or provided from heterologous sources by recombinant DNA techniques. Such sequences include nuclear localization sequences (NLS) known in the art.

"Animal" as used herein may be defined to include human, domestic (cats, dogs, etc.), agricultural (cows, horses, sheep, goats, chicken, fish, etc.) or test species (frogs, mice, rats, rabbits, simians, etc.).

Since the list of technical and scientific terms cannot be all encompassing, any undefined terms shall be construed to have the same meaning as is commonly understood by one of skill in the art to which this invention belongs. Furthermore, the singular forms "a", "an" and "the" include plural referents unless the context clearly dictates otherwise. For example, reference to a "restriction enzyme" or a "high fidelity enzyme" may include mixtures of such enzymes and any other enzymes fitting the stated criteria, or reference to the method includes reference to one or more methods for obtaining cDNA sequences which will be known to those skilled in the art or will become known to them upon reading this specification.

Before the present sequences, variants, formulations and methods for making and using the invention are described, it is to be understood that the invention is not to be limited only to the particular sequences, variants, formulations or methods described. The sequences, variants, formulations and methodologies may vary, and the terminology used herein is for the purpose of describing particular embodiments. The terminology and definitions are not intended to be limiting since the scope of protection will ultimately depend upon the claims.

Purified nucleotide sequences of this invention have numerous applications in techniques known to those skilled in the art of molecular biology. These techniques include their use as hybridization probes, for chromosome and gene mapping, in PCR technologies, in the production of sense or antisense nucleic acids. These examples are well known and are not intended to be limiting. Furthermore, the nucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

As a result of the degeneracy of the genetic code, a multitude of nucleotide sequences may be produced which are based upon the disclosed peptide, polypeptide, or protein encoding nucleotide sequences. Some of these will bear only minimal homology to the sequence disclosed herein; however his invention has specifically contemplated each and every possible variation of nucleotide sequence that could be made by selecting combinations based on possible codon choices. These combinations are made in accordance with the standard triplet genetic code as applied to the nucleotide sequence of naturally occurring peptide, polypeptide, or protein, and all such variations are to be considered as being specifically disclosed.

Although the peptide, polypeptide, or protein-encoding nucleotide sequences and their derivatives or variants are preferably capable of identifying the nucleotide sequence of the naturally occurring peptide, polypeptide, or protein under optimized conditions, it may be advantageous to produce peptide, polypeptide, or protein-encoding nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence without altering the encoded amino acid sequence include the production of RNA transcripts having more desirable properties, such as a longer half-life, than transcripts produced from the naturally occurring sequence.

Nucleotide sequences encoding a peptide, polypeptide, or protein may be joined to a variety of other nucleotide sequences by means of well established recombinant DNA techniques (Sambrook, J. et al. [1989] Molecular Cloning: A Laboratory Manual, Cold Spring Harbor Laboratory, Cold Spring Harbor, N.Y.; or Ausubel, F. M. et al. [1989] Current Protocols in Molecular Biology, John Wiley & Sons, New York City). Useful sequences include an assortment of cloning vectors such as plasmids, cosmids, lambda phage derivatives, phagemids, and the like. Vectors of interest include vectors for replication, expression, probe generation, sequencing, and the like. In general, vectors of interest may contain an origin of replication functional in at least one organism, convenient restriction endonuclease sensitive sites, and selectable markers for one or more host cell systems.

PCR as described in U.S. Pat. Nos. 4,683,195; 4,800,195; and 4,965,188 (hereby incorporated by reference in their entireties) provides additional uses for oligonucleotides based upon the peptide, polypeptide, or protein nucleotide sequences. Such oligomers are generally chemically synthesized, but they may be of recombinant origin or a mixture of both. Oligomers generally comprise two nucleotide sequences, one with sense orientation (5' to 3') and one with antisense (3' to 5') employed under optimized conditions for identification of a specific gene or diagnostic use. The same two oligomers, nested sets of oligomers, or even a degenerate pool of oligomers may be employed under less stringent conditions for identification and/or quantitation of closely related DNA or RNA sequences. Full length genes may be cloned utilizing partial nucleotide sequence and various methods known in the art. Gobinda et al. (Gobinda et al. [1993] *PCR Methods Applic* 2:318–22) disclose "restriction-site PCR" as a direct method which uses universal primers to retrieve unknown sequence adjacent to a known locus. First, genomic DNA is amplified in the presence of primer to linker and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR is the first method to report successful acquisition of unknown sequences starting with primers based on a known region (Triglia, T. et al. [1988] *Nucleic Acids Res* 16:8186). The method uses several restriction enzymes to generate a suitable fragment in the known region of a gene. The fragment is then circularized by intramolecular ligation and used as a PCR template. Divergent primers are designed from the known region. The multiple rounds of restriction enzyme digestions and ligations that are necessary prior to PCR make the procedure slow and expensive (Gobinda et al., supra).

Capture PCR (Lagerstrom M. et al. [1991] *PCR Methods Applic* 1:111–19) is a method for PCR amplification of DNA fragments adjacent to a known sequence in human and YAC DNA. This procedure is also useful, and generally applicable, in amplification of adjacent sequences surrounding known sequences in DNA originating from other animals, plants, and procaryotes. As noted by Gobinda et al., supra, capture PCR also requires multiple restriction enzyme digestions and ligations to place an engineered double-stranded sequence into an unknown portion of the DNA molecule before PCR. Although the restriction and ligation reactions are carried out simultaneously, the requirements for extension, immobilization and two rounds of PCR and purification prior to sequencing render the method cumbersome and time consuming.

Parker, J. D. et al. (1991; *Nucleic Acids Res* 19:3055–60), teach walking PCR, a method for targeted gene walking which permits retrieval of unknown sequences. PROMOTERFINDER is a kit available from Clontech Laboratories, Inc. (Palo Alto, Calif.) which uses PCR and primers derived from p53 to walk in genomic DNA. Nested primers and special PROMOTERFINDER libraries are used to detect upstream sequences such as promoters and regulatory elements. This process avoids the need to screen libraries and is useful in finding intron/exon junctions.

CLONTECH PCR-SELECT cDNA Subtraction (Clontech Laboratories, Inc., Palo Alto, Calif.) is yet another means by which differentially expressed genes may be isolated. The procedure allows for the isolation of transcripts present in one mRNA population which is absent, or found in reduced numbers, in a second population of mRNA. Rare transcripts may be enriched 1000-fold.

A method for analyzing either the size or the nucleotide sequence of PCR products is capillary electrophoresis. Systems for rapid sequencing are available from Perkin Elmer (Foster City Calif.), Beckman Instruments (Fullerton, Calif.), and other companies. Capillary sequencing employs flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (e.g., GENOTYPER and SEQUENCE NAVIGATORS from Perkin Elmer) and the entire process from loading of samples to computer analysis and electronic data display is computer controlled. Capillary electrophoresis provides greater resolution and is many times faster than standard gel based procedures. It is particularly suited to the sequencing of small pieces of DNA which might be present in limited amounts in a particular sample. The reproducible sequencing of up to 350 bp of M13 phage DNA in 30 min has been reported (Ruiz-Martinez, M. C. et al. [1993] *Anal Chem* 65:2851–8).

The terms "hybridize" or "hybridizing" refer to the binding of two single-stranded nucleic acids via complementary base pairing. The phrase "hybridizing specifically to" refers to binding, duplexing, or hybridizing of a molecule to a nucleotide sequence under stringent conditions when that sequence is present in a preparation of total cellular DNA or RNA.

In addition to polynucleotide sequences specifically exemplified herein, the present invention also concerns polynucleotide sequences that hybridize to the subject sequences. Preferably, the sequences hybridize under stringent hybridization conditions. The term "stringent conditions" refers to conditions under which a polynucleotide molecule will hybridize to another sequence, but not to sequences having little or no homology to the polynucleotide. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.1 to 1.0 N Na ion concentration at a pH of about 7.0 to 7.5 and the temperature is at least about 60° C. for long sequences (e.g., greater than about 50 nucleotides) and at least about 42° C. for shorter sequences (e.g., about 10 to 50 nucleotides).

The fim N polynucleotides, fim N polypeptides, fim N proteins, and fragments of fim N polynucleotides, polypeptides, proteins also encompass variant sequences containing mutations in the exemplified sequences; however, the variant fim N polynucleotides and fim N polypeptides, fim N proteins, and fragments of fim N must also increase the binding of attachment-deficient *B. bronchiseptica* to epithelial cells when expressed in said attachment-deficient cells. The mutations in nucleotide or amino acid sequences of the polynucleotides and polypeptides of the invention, respectively, can include, for example, nucleotide or amino acid substitutions, insertions, and deletions as long as the variant sequence has substantial sequence identity with an exemplified sequence of the present invention. Preferably, this sequence identity is greater than about 75%; more preferably, the sequence identity is greater than about 90%; and, most preferably, the sequence identity is greater than about 95%. A person skilled in the pertinent art can readily prepare and use variant polynucleotide sequences and polypeptide sequences of the present invention. As used herein, the term "sequence identity" refers to the homology between two distinct sequences as determined using, for example, the GCG FASTA software program (University of Wisconsin).

All patents, patent applications, provisional applications, and publications referred to or cited herein are incorporated by reference in their entirety to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Identification of fim N

The origin of the *B.bronchiseptica* strains has been previously described (Burns, E. H. Jr., J. M. Norman, M. D. Hatcher and D. A. Bemis [1993] *J. Clin. Microbiol.* 31: 1838–1844). Bordetella were grown in Brucella Broth, Brucella Agar (Difco) or Bordet-Gengou (BG) Agar prepared from BG base (BBL) with 15% horse blood. All strains were grown for 48 hours at 37° C. *Escherichia coli* were grown in LB Agar (Miller formulation) or broth (Difco) containing 50 μg/ml Ap or 15 μg/ml Tc for selection of bacteria carrying pBluescript based or pLAFR1 based plasmids, respectively.

The fim N gene was identified in a cosmid produced from *B. bronchiseptica* genomic DNA that restored adherence to an adhesion deficient *B. bronchiseptica* isolate (Burns [1995] supra). The presence of a fimbrial gene within the cosmid was predicted by hybridization with oligonucleotide probes representing highly conserved regions common to previously sequenced fimbrial genes. These probes were used to prepare a restriction map identifying the location of the fimbrial gene within the cosmid.

EXAMPLE 2
FimN Sequencing and Expression (Cosmid Gene)

Direct sequencing from cosmid DNA was used to determine the entire sequence of the putative protein coding region of the fim N gene and a portion of the promoter region. PCR generated amplicons used for subcloning were sequenced to ensure that they contained DNA identical to the gene identified in the cosmid. DNA sequencing was performed using an Applied Biosystems 373A automated sequencer.

The protein coding portion of the gene was produced as a PCR amplicon with restriction enzyme sites engineered at each end to facilitate cloning, in frame, in a bacterial expression vector. Restriction endonuclease fragments, products of HindlIl and Sall digests, were isolated from agarose gels using a QiaQuick Kit (Qiagen, Inc.). These fragments were cloned into pMAL expression vector (New England BioLabs) designed to produce fusion proteins with maltose binding protein. Transformation of competent *Escherichia coli* with recombinant plasmid DNA was carried out using Top 10F' One Shot cells (Invitrogen).

EXAMPLE 3
DNA Isolation and Characterization (Chromosomal Gene)

Chromosomal DNA was isolated from Brucella broth culture of *B. bronchiseptica* strain 110H using the method of Meade at al. (Meade, H. M., S. R. Long, G. B. Ruvkun, S. E. Brown, and F. M. Ausubel [1982] *J. Bacteriol.* 149:114–122). It was partially digested with EcoRI and 25–30 kb fragments were isolated on a 10–40% sucrose gradient (Maniatis, T., E. F. Fritch, and J. Sanbrook [1982] *Molecular cloning:* a laboratory manual. Cold Spring Harbor, N.Y.: Cold Spring Harbor Laboratory). These fragments were ligated to EcoRI-digested, calf intestinal phosphatase treated (Maniatis et al. [1982] supra) pLAFR1 DNA (Friedman, A. M., S. R. Long, S. E. Brown, W. J. Buikerman, and F. M. Ausebel [1982] *Gene* 18:289–296) and transformed into *E.coli* DH-1. The transformation reaction was plated on LB agar containing 15 $\mu$g/ml tetracycline to select for bacteria containing the cosmid pLAFR1. The library was probed via colony blot with a digoxigenin labeled oligo (GAY GAY GGC ACC ATC GTC ATC ACC GGC AC [SEQ ID NO:18]), designed by Mooi et al. (1987) to correspond to the nt sequence encoding the first ten N-terminal aa acids of the *Bordetella pertussis* serotype 2 fimbrial subunit.

Colonies which carried plasmids that hybridized with this probe were selected and plasmid DNA was isolated. The reactive plasmids included pGB710, with a 25 kb insert, and pGB84, containing a 20 kb insert. pGB84 was digested with EcoRI and a 4.5 kb fragment was subcloned into pBluescript and designated pBS84. A BamHI fragment from pBS84 was subsequently cloned into the BamHI site in pCRII (Invitrogen) and designated pCR2bam. DNA corresponding to an ORF of a putative fimbrial protein was amplified by PCR using primers containing restriction enzyme sites to facilitate cloning. The forward and reverse primers were, respectively, 5'-GGGAATTCACGATCGTGATCACCGGCA-3' (SEQ ID NO:19) and 5'-GGCTCGAGGATTATCCTTATCAAGCC-3'(SEQ ID NO:20). A 30 cycle program consisted of denaturing at 95° C. for 1.5 minutes, annealing at 50° C. for 30 seconds, and extension at 72° C. for one minute. This was followed in the last cycle by five minutes of extension at 72° C. The PCR products were resolved by electrophoresis on 1.25% agarose gels containing EtdBr. Gels were viewed and photographed under ultraviolet light. The PCR products were digested with EcoRI and XhoI and cloned into pPROEXHTa (GIBCO-BRL) vector for expression of the recombinant fimbrial protein with a polyhistidine tag. The plasmid DNA and PCR fragments were ligated and tansformed into *E. coli* BL-21 gold endA (Stratagene) (Maniatis et al., 1982).

EXAMPLE 4

DNA Sequencing and Analysis (Chromosomal Gene)

All plasmid and cosmid DNA for sequencing was isolated using Qiagen Plasmid Midi Kits according to the manufacturer's instructions (Qiagen). Initial sequencing was done with pCR2bam using M13 and T7 primers complementary to pCR2.1 or pCRII DNA flanking *B. bronchiseptica* inserts. To obtain sequence information for the ORF 3' to this insert, direct sequencing was done from pBS84 using primers designed from the 3' end of the pCR2bam sequence. The ORF and putative promoter region were sequenced directly from pGB710 using primers designed from the pBS84 and pCR2bam derived sequences. *B. bronchiseptica* chromosomal DNA, isolated using the Easy-DNA kit (Invitrogen), was amplified by PCR as described above using 5'-GGAAGCTTGCCATCACCAACTTATGTG-3' (SEQ ID NO:1) and 5'-GGGAATTCGATTATCCTTATCAAGCCC-3' (SEQ ID NO:2) as the forward and reverse primers, respectively. Sequencing was done with the Applied Biosystems dye terminator kit and Applied Biosystems 373 DNA sequencer at the University of Tennessee Molecular Biology Core Facility. Analysis of DNA sequences was done using Wisconsin Package Version 9.1, Genetics Computer Group (GCG). Pair-wise comparisons of fimN with other *Bordetella bronchiseptica* fimbrial gene sequences was done using the Gap program of the Genetics Computer Group (GCG) software package. Gap uses the alignment method of Needleman and Wunsch (*J. Mol. Biol.* [1970] 48:443–453). The Gap program considers all possible alignments and gap positions and creates the alignment with the largest number of matched bases and the fewest gaps. Our analysis was done using a gap creation penalty of 50 and gap extension penalty of 3.

*B. bronchiseptica* DNA obtained from plasmids pBS84 and pGB710 and chromosomes from strains 110H and 64-C-0406 (FIG. 4) contained the fimN ORF predicted to encode a 209 aa protein The fimN protein had significant homology with *B. bronchiseptica* and *B. pertussis* fimbrial subunits fim2, fim3 and fimX (FIG. 5). FimN contained a stretch of cytosine residues ending at nt −60, similar in length to those of other fimbrial genes expressed by Bordetella species (FIG. 6). The promoter region had a sequence motif corresponding to a previously identified activator binding region, located upstream from the C-stretch, that closely resembles a similar region in fim2,fim3, and fimX (Riboli et al. [1991] supra) FIG. 6). DNA sequences corresponding to fimN were obtained from *B. bronchiseptica* chromosomal DNA isolated from stain 110H, the strain from which pBS84 and pGB710 were derived, and an unrelated virulent strain 64-C-0406 (FIGS. 4 and 6). The chromosomal DNA sequences of fimN matched exactly with the DNA sequence of plasmid derived fimN except that both chromosomal DNAs contained two additional cytosine residues in their C-stretches (FIG. 6). BLAST analysis (Altschul, S. F., W. Gish, W. Miller, E. W. Myers, and D. J. Lipman [1990] *J. Mol. Biol.* 215:403–410) of the fimN encoded protein sequence showed that, among all available protein sequences, the predicted fimN protein had greatest homology with fimbrial proteins from *B. bronchiseptica* and *B. pertussis*.

EXAMPLE 5
Recombinant Protein Expression (Maltose Fusion Protein)

Recombinants were grown overnight in LB-ampicillin containing 100 µg/ml ampicillin, inoculated into Rich Media (New England BioLabs) and incubated until an OD of $A_{600}$~0.5 was achieved. Protein expression was induced with IPTG for 2 Hours. Fimbrial proteins were extracted from cells using a combination of sonication and B-PER Bacterial Protein extraction Reagent (Pierce).

Fusion proteins were isolated by affinity chromatography using amylose coupled to agarose for pMAL. Samples were eluted with maltose and serial fractions were collected and the 280 nm O.D. of the eluate was monitored. Peak samples were pooled and saved for further analysis.

EXAMPLE 6
Conjugation into *B. bronchiseptica*

Plasmids were transferred to *B. bronchiseptica* strains by tri-parental mating (Weiss, A. A. and S. Falkow [1982] *J. Bacteriol.* 152:549–552) and *B. bronchiseptica* carrying pGB710 was selected on Brucella agar with 15 µg/ml Tc and 20 µg/ml furaltadone. Bacteria were maintained on medium containing Tc only.

EXAMPLE 7
Expression of Recombinant FimN (Polyhistidine Fusion Protein)

The PCR products described above were digested with EcoRI and XhoI and cloned into pPROEXHTa (GIBCO-BRL) vector for expression of the recombinant fimbrial protein with a polyhistidine tag. Expression of recombinant fimN protein was induced from cultured bacteria, transformed with the plasmid, by the addition of IPTG to a final concentration of 0.6 mM for a period of 2.5 hours. The recombinant fusion protein was purified under denaturing conditions according to the manufacturer's protocol (Qiagen). The bacteria were lysed with 8 mM urea buffer, pH 8.0 and the supernatant was exposed to Ni—NTA resin, washed two times with urea buffer, pH 6.3, and bound recombinant protein was eluted with urea buffer, pH 5.9. The sample was dialyzed extensively with PBS, pH 7.0. Recombinant protein was resolved by SDS-PAGE and stained with Coomassie blue (GelCode Blue Stain; Pierce).

Fim N protein expressed from pPROEXHTa and isolated with Ni—NTA resin produced a band on polyacrylamide gels of approximately 26,500 daltons. This size was consistent with the 22,098 dalton value predicted from the sequence of the fimN gene plus the addition of aa encoded by the expression vector.

EXAMPLE 8
Recombinant Protein Characterization (MBP Fusion Protein)

SDS-PAGE was performed in 10% acrylamide gels. The vector derived fusion moiety maltose binding protein (MBP) was cleaved to separate it from fim N protein using Factor Xa. Cleaved and uncleaved fusion proteins as well as MBP standard were run on gels for protein size comparison.

A recombinant chimeric protein was produced to evaluate a vaccine based upon key virulence factors from two organisms important in the respiratory disease of livestock. A 663 bp fragment containing a neutralizing epitope of *Pasteurella hemolytica* leukotoxin was combined with a *Bordetella bronchiseptica* fimbrial protein gene (fim N). The recombinant gene was cloned in PGEX vector under the control of the TAC promoter and expressed in 72 Kd fusion protein was affinity purified using glutathione sepharose and evaluated by SDS-PAGE, western blots, and ELISA. A single band was visible on coomassie stained polyacrylamide gels and western blots probed with antibodies reactive with fimbrial protein and *P. hemolytica* leukotoxin. Strong antibody reactivity was obtained in ELISA assays when the recombinant protein antigen was reacted with the same antibodies. Immunization of rabbits and mice with the recombinant protein elicited a strong antibody response to both of the antigens. Serum leukotoxin neutralizing activity was significantly higher in animals immunized with LTX-FIM than with all other combinations of LTX recombinants and adjuvants tested. These results suggest that the recombinant protein is a good candidate for a respiratory disease vaccine, the components of which, may have a synergistic effect in eliciting a protective immune response.

EXAMPLE 9
Vaccines

The novel fim N polypeptides described herein can be used advantageously in an immunogenic composition such as a vaccine. Such a composition, when administered to an animal or person, raises antibodies or other immune responses which reduce the susceptibility of that animal or human to Bordetella infection.

Vaccines comprising the fim N polypeptides disclosed herein, and variants thereof having antigenic immunogenicproperties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used. In the case of peptides, coupling to larger molecules such as KLH or tetanus toxoid sometimes enhances immunogenicity. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The compounds can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered can depend on the subject to be treated and the degree of protection desired. The fim N polypeptides of the subject invention may be combined with carbohydrate antigenic components to enhance the immunogenic response and provide a broader range of protection. The combination may be, for example, through chemical coupling. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

Alternatively, the polynucleotides can be formulated into compositions useful for nucleic acid vaccinations. Nucleic acid vaccination has been shown to induce protective immune responses in non-viral systems and in diverse animal species (Special Conference Issue, WHO meeting on nucleic acid vaccines [1994] *Vaccine* 12:1491). Nucleic acid vaccination has induced cytotoxic lymphocyte (CTL), T-helper 1, and antibody responses, and has been shown to be protective against disease (Ulmer, J., J. Donelly, S. Parker et al. [1993] *Science* 259:1745). For example, direct intramuscular injection of mice with DNA encoding the influenza nucleoprotein caused the production of high titer antibodies, nucleoprotein-specificCTLs, and protection against viral challenge. Immunization of mice with plasmid DNA encoding the *Plasmodium yoelii* circumsporozoite protein induced high antibody titers against malaria sporozoites and CTLs, and protection against challenge infection (Sedegah, M., R. Hedstrom, P. Hobart, S. Hoffman [1994] *Proc. Natl. Acad. Sci. USA* 91:9866). Cattle immunized with plasmids encoding bovine herpesvirus 1 (BHV-1) glycoprotein IV developed neutralizing antibody and were partially protected (Cox, G., T. Zamb, L. Babiuk [1993] *J. Virol.* 67:5664).

Compositions comprising the subject polynucleotides can include appropriate nucleic acid vaccine vectors (plasmids), which are commercially available (e.g., Vical, San Diego, Calif.). The subject polynucleotides which may be inserted into commercially available vectors may encode fragments or variants of the fim N protein which induce an immune response. In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science,* Mack Publishing Company, Easton, Pa.

In one embodiment of the subject invention, the polynucleotide vaccines are administered in conjunction with an antigen. In a preferred embodiment, the antigen is the polypeptide which is encoded by the polynucleotide administered as the polynucleotide vaccine (fim N). As a particularly preferred embodiment, the antigen is administered as a booster subsequent to the initial administration of the polynucleotide vaccine. In another embodiment of the invention, the polynucleotide vaccine is administered in the form of a "cocktail" which contains at least two of the polynucleotides of the subject invention. The "cocktail" may be administered in conjunction with an antigen or an antigen booster as described above. The polynucleotide vaccine compositions of the subject invention may also be administered alone.

EXAMPLE 10

ELISA with Recombinant fimN

Affinity purified fimN protein was diluted in PBS to a concentration of 10 $\mu$g/ml and coated on Immulon2 microtiter plates (Dynex) by the addition of 100 $\mu$L per well. After binding overnight at 4° C., unbound antigen was removed by washing three times with 150 $\mu$L of PBS containing 0.05% PBSTW. The plates were then washed and mAB reactive with Bordetella fimbriae were added, 100 $\mu$L into duplicate wells, and incubated at 37° C. for 1 hour. The plates were washed and affinity purified, peroxidase conjugated anti-mouse IgG was added, 100 $\mu$L per well, and incubated for 1 hour at 37° C. The plates were washed and then received 100 $\mu$L of 2,2'-azino-bis(2-ethylbenzthiazoline-6-sulfonic acid) substrate dissolved in 0.05M phosphate-citrate buffer, pH 5.0. The optical density of the solution in each well was determined at 405 nm. Positive samples were determined as those with optical densities greater than twice the value of samples that did not receive mAb.

mAB BpA5, BpA10, BpC4, and BpH2, produced against Bordetella fim2 subunits, (Kindly provided by Michael J Brennan, Laboratory of Pertussis, Center for Biologics Evaluation and research, Bethesda, Md.) reacted with fimN recombinant protein in ELISA assays. mAb CF8, reactive with fim2 polymers, but not monomers (Burns et al. [1993] supra), did not react with fimN recombinant protein.

EXAMPLE 11

Attachment Assay

Attachment assays were performed using African green monkey kidney cells (Vero). Vero cells were grown to confluency in Dulbecco's Modified Eagle's Medium (DMEM; CellGro, CellGenix) with 10% fetal bovine serum (FBS; CellGro). All media were supplemented with 200 mM glutamine, 30 $\mu$g/ml methionine, 50 units/ml penicillin, 50 $\mu$g/ml streptomycin, and 125 ng/ml amphotericin B. Confluent cells were detached from the tissue culture flasks using 0.25% Trypsin/0.1% EDTA (CellGro) and split 1:4 into 8 well glass chamber slides (LabTek) with each well receiving 200 $\mu$l of cells suspended in medium. Slides were incubated overnight at 37° C. with 5% $CO_2$.

*B. bronchiseptica* strains were grown on BG agar for 3 days. Domed hemolytic colonies were selected and used to inoculate a Brucella agar plate which was grown 24 hours. Colonies from this plate were diluted in the appropriate cell culture medium to a 595 nm O.D. of 0.1. 200 $\mu$l of the bacterial suspension was added to each well of the chamber slides containing the tissue culture cells. Cells with bacteria were incubated for 1 hour at 37° C. with 5% $CO_2$. After incubation, the slides were washed three times with Hank's Balanced Salt Solution to remove any non-adherent bacteria.

Slides were fixed in 95% ethanol for 1 minute. The slides were then stained with a 1:2 dilution of Gram's Crystal Violet for 1 minute. For each well, the number of bacteria attached to 50 cells was determined microscopically. Assays were performed in triplicate.

In the attachment assays (FIG. 7) *B.bronchiseptica* strain 110H exhibited strong binding to Vero cells. Strain 110NH, a spontaneous, avirulent phase mutant of 110H, bound weakly to Vero cells. *B.bronchiseptica* R-5, another virulent strain, attached at levels intermediate to those of 110H and 110NH. Introduction of pGB710 into R-5 resulted in increased attachment to Vero cells to levels comparable to those of 110H. Plasmid pLAFR1 vector alone, without *B.bronchiseptica* fimbrial insert, had no effect on the binding properties of R-5. pGB710 did not alter the attachment properties of 110H or 110NH. The introduction of the cosmid containing the fimN gene also reconstituted adherence in R-5, an adherence deficient strain expressing the Bvg+ phenotype. Introduction of the cosmid into a bvg– mutant of *B. bronchiseptica* did not appear to resonstitute adherence.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide fragment encoding fim N of Bordetella bronchiseptica, or a fragment of fim N, wherein said fim N encodes a protein having at least about 75% sequence identity as compared to the amino acid sequence as set forth in SEQ ID NO:4; and wherein said fim N or fragment of fim N, increases the binding of attachment-deficient Bordetella bronchiseptica to epithelial cells when expressed in said attachment-deficient cells.

2. The polynucleotide according to claim 1, wherein said polynucleotide encodes the protein having at least about 75% sequence identity with the amino acid sequence of SEQ ID NO:3.

3. An isolated polynucleotide fragment encoding a fim N polypeptide of Bordetella bronchiseptica, wherein said polypeptide comprises amino acid residues 28 to 209 of SEQ ID NO:4.

4. The polynucleotide of claim 1, wherein said polynucleotide fragment encodes a polypeptide having at least about 90% sequence identity with the amino acid sequence of SEQ ID NO:3.

5. The polynucleotide of claim 1, wherein said polynucleotide fragment encodes a polypeptide having about 95% sequence identity with the amino acid sequence of SEQ ID NO:3.

6. The polynucleotide of claim 1, wherein said polynucleotide encodes a polypeptide comprising the amino acid sequence of SEQ ID NO:4.

7. The polynucleotide of claim 1, wherein said polynucleotide comprises SEQ ID NO:3.

8. The polynucleotide of claim 1 or 3, further comprising at least one heterologous polynucleotide sequence.

9. The polynucleotide of claim 8, wherein said heterologous sequence is a vector.

10. The polynucleotide of claim 8, wherein said heterologous sequence encodes a heterologous protein or antigen.

11. The polynucleotide of claim 10, further comprising a vector.

12. The polynucleotide of claim 10, wherein said heterologous sequence encodes a leucotoxin.

13. A transformed host comprising the polynucleotide sequence of claim 1 or 3, wherein said host is selected from the group consisting of microorganisms, eukaryotic cells, plant cells and viruses.

14. A probe or primer comprising a sequence selected from the group consisting of:

a) GGAAGCTTGCCATCACCAACTTATGTG (SEQ ID NO:1);

b) GGAATTCGATTATCCTTATCAAGCCC (SEQ ID NO:2); and c) the complement of SEQ ID NO:1 or SEQ ID NO:2.

15. The probe or primer of claim 14, further comprising a label.

* * * * *

UNITED STATES PATENT AND TRADEMARK OFFICE
CERTIFICATE OF CORRECTION

PATENT NO. : 6,475,754 B1
DATED : November 5, 2002
INVENTOR(S) : David A. Bemis, Stephen A. Kania and Robert N. Moore It is certified that error appears in the above-identified patent and that said Letters Patent is hereby corrected as shown below:

Column 1,
Line 18, "regulated by by genes." should read -- regulated by bvg genes. --.

Signed and Sealed this

Twenty-ninth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,475,754 B1
DATED : November 5, 2002
INVENTOR(S) : David A. Bemis, Stephen A. Kania and Robert N. Moore It is certified that error appears in the above-identified patent and that said Letters Patent is hereby corrected as shown below:

<u>Column 2,</u>
Line 60, "regulated by by genes." should read -- regulated by bvg genes. --.

This certificate supersedes Certificate of Correction issued July 29, 2003.

Signed and Sealed this

Twenty-sixth Day of August, 2003

JAMES E. ROGAN
*Director of the United States Patent and Trademark Office*